US010732186B2

(12) United States Patent
Chorev et al.

(10) Patent No.: US 10,732,186 B2
(45) Date of Patent: Aug. 4, 2020

(54) METHODS AND REAGENTS FOR THE ASSESSMENT OF GESTATIONAL DIABETES

(71) Applicant: President and Fellows of Harvard College, Cambridge, MA (US)

(72) Inventors: Michael Chorev, Chestnut Hill, MA (US); Jose Alberto Halperin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 346 days.

(21) Appl. No.: 15/100,563

(22) PCT Filed: Dec. 3, 2014

(86) PCT No.: PCT/US2014/068426
§ 371 (c)(1),
(2) Date: May 31, 2016

(87) PCT Pub. No.: WO2015/084994
PCT Pub. Date: Jun. 11, 2015

(65) Prior Publication Data
US 2016/0299150 A1    Oct. 13, 2016
US 2017/0108505 A2    Apr. 20, 2017

Related U.S. Application Data

(60) Provisional application No. 61/946,373, filed on Feb. 28, 2014, provisional application No. 61/945,860, filed on Feb. 28, 2014, provisional application No. 61/911,306, filed on Dec. 3, 2013.

(51) Int. Cl.
| | |
|---|---|
| *G01N 33/68* | (2006.01) |
| *A61K 39/395* | (2006.01) |
| *A61K 49/14* | (2006.01) |
| *A61K 49/16* | (2006.01) |
| *G01N 33/566* | (2006.01) |

(52) U.S. Cl.
CPC ......... *G01N 33/689* (2013.01); *G01N 33/566* (2013.01); *G01N 2333/70596* (2013.01); *G01N 2400/02* (2013.01); *G01N 2440/38* (2013.01); *G01N 2800/042* (2013.01); *G01N 2800/368* (2013.01)

(58) Field of Classification Search
CPC ............... G01N 33/566; G01N 33/689; G01N 2333/70596; G01N 2800/042; G01N 2400/02; G01N 2440/38; G01N 2800/368
See application file for complete search history.

(56) References Cited

U.S. PATENT DOCUMENTS

| | | | |
|---|---|---|---|
| 4,950,712 A | 8/1990 | Letourneur et al. | |
| 5,248,832 A | 9/1993 | Lee | |
| 5,478,741 A * | 12/1995 | Maret | C07K 14/445 435/34 |
| 5,670,377 A | 9/1997 | Peterson et al. | |
| 7,439,330 B2 * | 10/2008 | Halperin | G01N 33/566 435/7.9 |
| 8,298,779 B2 | 10/2012 | Halperin | |
| 8,404,451 B2 | 3/2013 | Halperin | |
| 2004/0166531 A1 | 8/2004 | Halperin | |
| 2013/0189711 A1 | 7/2013 | Halperin | |
| 2014/0322723 A1 | 10/2014 | Halperin et al. | |
| 2015/0315286 A1 | 11/2015 | Halperin et al. | |
| 2017/0023589 A1 | 1/2017 | Chorev et al. | |
| 2017/0199201 A2 * | 7/2017 | Chorev | G01N 33/6893 |

FOREIGN PATENT DOCUMENTS

| | | |
|---|---|---|
| WO | WO-2006/009533 A1 | 1/2006 |
| WO | WO-2008/137165 A1 | 11/2008 |
| WO | WO-2012/109538 A2 | 8/2012 |

OTHER PUBLICATIONS

Hass et al. The Sodium Borohydride digest 2003, Rohm and Hass Company, 60 Willow St., PA. (Year: 2003).*
Ghosh et al., "A Specific and Sensitive Assay for Blood Levels of Glycated Cd59: A Novel Biomarker for Diabetes," available in PMC Aug. 1, 2014, published in final edited form as: Am J Hematol. 88(8): 670-676 (2014) (15 pages).
Extended European Search Report for International Application No. PCT/US2014/068426, dated May 23, 2017 (9 pages).
Ghosh et al., "Plasma Glycated CD59, a Novel Biomarker for Detection of Pregnancy-Induced Glucose Intolerance," Diabetes Care. pp. 1-4 (2017) (4 pages).
International Search Report and Written Opinion for International Application No. PCT/US2014/068426, dated Mar. 30, 2015 (14 pages).
International Preliminary Report on Patentability for International Application No. PCT/US2014/068426, dated Jun. 16, 2016 (7 pages).
Qin et al., "Glycation Inactivation of the Complement Regulatory Protein CD59," Diabetes. 53(10): 2653-2661 (2004).
Office Action and English Translation for Russian Patent Application No. 2016123659, dated Feb. 7, 2019 (15 pages).
Moskva, "Solvents in organic chemistry," Soros Educational Journal. 4:44-50 (1999) (8 pages).
Kaur et al., "Antibody Promiscuity: Understanding the Paradigm Shift in Antigen Recognition," IUBMB Life. 67(7):498-505 (2015) (8 pages).
"Product Specification for Sodium borohydride solution—0.5 M in 2-methoxyethyl ether," Sigma-Aldrich (1 page).
"I. Properties," *Sodium Borohydride Digest*. John Yamamoto, Rohm and Haas Company, 6-13 (2003).
"PubChem Compound Summary for CID 8150—Diglyme," <https://pubchem.ncbi.nlm.nih.gov/compound/Diglyme>, retrieved on Dec. 14, 2017 (3 pages).

* cited by examiner

Primary Examiner — Shafiqul Haq
(74) Attorney, Agent, or Firm — Clark & Elbing LLP

(57) ABSTRACT

The invention involves assays, diagnostics, kits, and assay components for determining levels of glycated CD59 in the assessment of gestational diabetes mellitus and/or related disorders and/or conditions.

4 Claims, 4 Drawing Sheets
Specification includes a Sequence Listing.

METHODS AND REAGENTS FOR THE ASSESSMENT OF GESTATIONAL DIABETES

GOVERNMENT SUPPORT

This invention was made with government support under Grant No. DK095429-01 awarded by the National Institutes of Health. The United States government has certain rights in the invention.

REFERENCE TO A SEQUENCE LISTING

This application contains a Sequence Listing in computer readable form. The computer readable form is incorporated herein by reference.

BACKGROUND OF THE INVENTION

Diabetes is characterized by elevated blood glucose levels. Sustained elevation of blood glucose levels may affect proteins by a process known as glycation. Glycation is the non-enzymatic attachment of glucose to proteins and is considered a major pathophysiological mechanism causing tissue damage in diabetic subjects. Glycation involves the reaction of glucose and/or other reducing sugars with amino groups in proteins resulting in the formation of a Schiff base or aldimine. This labile adduct can tautomerize via the Amadori rearrangement to the more stable ketoamine.

Different glycated proteins have been identified in diabetic subjects, including albumin, hemoglobin and others. The function of glycated proteins may be impaired, depending on the location of the amino group(s) affected. For example, amino-terminal glycation of the 3-chains of hemoglobin gives rise to the glycated hemoglobins (HbA1c) in which responsiveness to 2,3-diphosphoglycerate is decreased and oxygen affinity increased. Glycation of the major thrombin inhibitor of the coagulation system, antithrombin III, decreases its affinity for heparin, and has been postulated to contribute to the hypercoagulable state associated with diabetes.

Measurement of the extent of protein "glycation" of certain proteins may be a valuable clinical tool to provide a more stable indicator of glycemic control than shorter term indicators such as measuring glucose levels directly, ultimately helping to improve the efficacy of treatments. The present inventors have previously shown that K41 glycation of CD59 is correlated to abnormal blood sugar levels and that glycation at K41 interferes with the normal activity of CD59 (U.S. Pat. Nos. 6,835,545; 7,049,082; and 7,439,330; the entire contents of each of which are incorporated herein by reference).

There remains, however, a need for improved methods of detecting and diagnosing diabetic conditions. In particular, certain patient populations may benefit from such improved methods. One such patient population includes pregnant women, who are at risk of developing gestational diabetes.

SUMMARY OF THE INVENTION

In some embodiments, the present invention provides a kit for determining the concentration of GCD59 in a subject sample. Such subject samples may be obtained from a pregnant subject. Kits may optionally comprise one or more internal controls. Some kits comprise a capture antibody capable of associating with a capture epitope on CD59, wherein said capture epitope may lack lysine residue number 41 (K41). Kits may also comprise a detection antibody capable of associating with a detection epitope on CD59. Such detection epitopes may comprise glycated K41. Kits of the present invention may also comprise a protein standard. In some cases, kits may comprise packaging and instructions for use thereof.

In some embodiments, capture epitopes may comprise an amino acid sequence with at least 70% identity to that of SEQ ID NO:2. In some cases capture epitopes may comprise an amino acid sequence with at least 85% identity to that of SEQ ID NO:4. Capture antibodies disclosed herein may be generated using a capture antibody peptide antigen comprising at least 70% identity to the amino acid sequence of SEQ ID NO:2. Other capture antibodies may be generated using a capture antibody peptide antigen comprising at least 85% identity to the amino acid sequence of SEQ ID NO:4. Further capture antibodies may be generated using a capture antibody peptide antigen comprising an amino acid sequence selected from the group consisting of SEQ ID NOs:3-6. Capture antibody peptide antigens may comprise one or more non-natural amino acids. Such capture antibody peptide antigens may comprise the amino acid sequence of SEQ ID NO:7 or SEQ ID NO:8. In some cases, capture antibody peptide antigens may be cyclic.

In some embodiments, detection epitopes may comprise glycated K41 comprising a chemical structure selected from the group consisting of structures I-VII presented hereinbelow. Detection epitopes may comprise an amino acid sequence with at least 70% identity to that of SEQ ID NO:9. Detection antibodies may be generated using a detection antibody peptide antigen comprising an amino acid sequence selected from the group consisting of SEQ ID NOs:9-11. Protein standards of the present invention may comprise surrogate compounds, said surrogate compounds comprising a capture domain, wherein said capture domain associates with said capture antibody, and a detection domain, wherein said detection domain associates with said detection antibody. Capture domains of surrogate compounds may comprise an amino acid sequence selected from the group consisting of SEQ ID NOs:2-8. Detection domains of surrogate compounds may comprise an amino acid sequence selected from the group consisting of SEQ ID NOs:9-11. Detection domains may further comprise a glycated lysine residue. Such glycated lysines may comprise a chemical structure selected from the group consisting of structures I-VII presented hereinbelow. Surrogate compounds may comprise a detection domain and capture domain joined by a linker. Such linkers may comprise polyethylene glycol. Linkers may comprise a structure according to structure VIII, presented hereinbelow.

In some embodiments, kits of the present invention may comprise one or more reducing agents for reducing subject samples. Such reducing agents may comprise sodium borohydride. In some cases, sodium borohydride may be provided as part of a reducing agent solution. Such solutions may comprise water and/or one or more organic solvent. In some embodiments, organic solvents may be selected from triethylene glycol dimethyl ether, tetraglyme and bis(2-methoxyethyl) ether. Sodium borohydride may be present in reducing agent solutions at a concentration of from about 0.1 M to about 10 M.

Antibodies of the present invention may be monoclonal or polyclonal antibodies. Monoclonal antibodies may be derived from mouse or rabbit cells. Antibodies may also comprise one or more detectable label. Secondary detection antibodies may be linked to horseradish peroxidase (HRP). Kits comprising such antibodies may comprise an HRP substrate for colorimetric quantification.

Methods of the present invention may include a method for determining the concentration of GCD59 in one or more samples from a pregnant subject comprising obtaining one or more samples from a pregnant subject during one or more gestational window and using a kit described herein to determine the concentration of GCD59. Samples according to such methods may include bodily fluid samples selected from the group consisting of blood, urine, mucous, amniotic fluid and saliva. Some samples may comprise a combination of at least one blood sample and one or more other bodily fluid samples. According to some methods, a single blood sample may be used. According to some methods, gestational windows may comprise from about 20 to about 36 weeks of pregnancy. In some cases, samples may be taken after a glucose challenge.

In some embodiments, the present invention provides methods of diagnosing gestational diabetes mellitus (GDM) in a subject comprising obtaining one or more samples from a subject during one or more gestational window, using a kit to determine the concentration of GCD59 in such samples and providing a diagnosis of GDM if the concentration of GCD59 is greater than a predetermined cut-off value. In some cases, such methods may be carried out without the need for consumption restrictions and/or requirements. Samples according to such methods may include bodily fluid samples selected from the group consisting of blood, urine, mucous, amniotic fluid and saliva. Some samples may comprise a combination of at least one blood sample and one or more other bodily fluid samples. According to some methods, a single blood sample may be used. According to some methods, gestational windows may comprise from about 20 to about 36 weeks of pregnancy. In some cases diagnosis of GDM may comprise diagnosis of a GDM subclass selected from the group consisting of Class A1, Class A2, Class B, Class C, Class D, Class F, Class R, Class H and Class T.

According to some methods of the present invention, diagnosis of GDM in subjects may be carried out by obtaining one or more samples from a subject during one or more gestational window, using a kit to determine the concentration of GCD59, comparing the concentration of GCD59 with the results of one or more other analyses of the subject and providing a diagnosis of GDM based on the comparison. Other analyses may comprise the level of one or more biomarkers selected from the group consisting of insulin, glucose and a glycated protein other than GCD59. Wherein such biomarkers comprise glucose levels, such levels may comprise fasting plasma glucose levels or random plasma glucose levels. Further analyses may comprise testing selected from the group consisting of glucose challenge testing, oral glucose tolerance testing (OGTT), fasting glucose testing, random glucose testing, 2-hour postprandial glucose testing, hemoglobin A1c (HbA1c) testing, fructosamine testing and 1,5-anhydroglucitol testing.

The disclosure herein further provides methods of diagnosing GDM in a subject, wherein such a subject presents with one or more preliminary indications of one or more risk factors for GDM. Such methods may comprise obtaining one or more samples from a subject during one or more gestational window, using a kit to determine the concentration of GCD59 in one or more subject samples and providing a diagnosis of GDM if the concentration of GCD59 is greater than a predetermined cut-off value. Preliminary indications according to such methods may comprise results from one or more tests, wherein such tests indicate that a subject presents with GDM. Such tests may include OGTT testing, fasting glucose testing, random glucose testing, 2-hour postprandial glucose testing, HbA1c testing, fructosamine testing and 1,5-anhydroglucitol testing. In some cases, preliminary indications may comprise one or more symptoms of GDM. Such symptoms may include thirst, fatigue, nausea, vomiting, bladder infection, yeast infection and blurred vision. Risk factors for GDM may include elevated body mass index (BMI), family history of diabetes, family history of prediabetes, family history of GDM, advanced maternal age, afflicted with polycystic ovary syndrome, history of smoking, history of obstetric issues, high cholesterol and short stature. Wherein subjects comprise elevated BMI, BMI categories may include overweight (BMI from about 25 to about 29.9 kg/m$^2$), grade I obesity (BMI from about 30 to about 34.9 kg/m$^2$), grade II obesity (BMI from about 35 to about 39.9 kg/m$^2$) and grade III obesity (BMI over 40 kg/m$^2$). Further risk factors may comprise the ethnicity of a subject. Such ethnicities may include, but are not limited to African American, Native American, Hispanic and South Asian.

In some embodiments, methods of the present invention may be used to assign a level of risk of developing GDM in a subject. Such methods may comprise obtaining one or more samples from a subject, using a kit to determine the concentration of GCD59 in such samples, comparing the concentration of GCD59 against two or more concentration ranges associated with two or more levels of risk of developing GDM, selecting a concentration range and associated level of risk of developing GDM that includes such a concentration of GCD59, and assigning to the subject a level of risk of developing GDM associated with the selected concentration range.

Some methods presented herein comprise assigning a level of GDM severity to one or more subjects afflicted with GDM comprising obtaining one or more samples from such subjects during one or more gestational window, using a kit to determine the concentration of GCD59 in the subject samples, comparing the concentration of GCD59 against two or more concentration ranges associated with two or more levels of GDM severity, selecting a concentration range and associated level of GDM severity that includes the determined concentration of GCD59 and assigning a level of GDM severity associated with the selected concentration range. Levels of GDM severity may be selected from the group consisting of mild, moderate and severe.

Also provided herein are methods of monitoring GDM in a subject afflicted with GDM comprising obtaining one or more samples during one or more gestational window from a subject afflicted with GDM, using a kit to determine the concentration of GCD59 in the samples, and comparing the concentration of GCD59 obtained to earlier obtained results. Such earlier obtained results may comprise results from testing selected from the group consisting of glucose challenge testing, OGTT testing, fasting glucose testing, random glucose testing, 2-hour postprandial glucose testing, HbA1c testing, fructosamine testing and 1,5-anhydroglucitol testing. Earlier obtained results may also comprise baseline GCD59 concentration values obtained using a kit. In some cases, samples may be obtained from about 2 weeks apart to about 2 months apart.

In some embodiments, the present invention provides a method of monitoring a diabetic condition in a postpartum subject comprising obtaining one or more samples from a postpartum subject, using a kit to determine the concentration of GCD59 in the samples, and comparing the concentrations of GCD59 to earlier obtained results. Such earlier obtained results may comprise results from testing selected from the group consisting of glucose challenge testing, OGTT testing, fasting glucose testing, random glucose testing, 2-hour postprandial glucose testing, HbA1c testing, fructosamine testing and 1,5-anhydroglucitol testing. Earlier obtained results may also comprise baseline GCD59 concentration values obtained using a kit. In some cases, samples may be obtained from about 2 weeks apart to about 2 months apart.

Included herein are methods of diagnosing pre-eclampsia in a subject comprising obtaining one or more samples from a subject, using a kit to determine the concentration of GCD59 in the samples, and providing a diagnosis of pre-eclampsia if the concentration of GCD59 is greater than a predetermined cut-off value. Also included are methods of reducing, reversing and/or preventing one or more GDM-related conditions in an infant subject comprising obtaining one or more samples during one or more gestational window from a subject pregnant with the infant subject, using a kit to determine the concentration of GCD59 in the samples, determining the risk, presence and/or progression of the GDM-related conditions in the infant subject using the determined concentration of GCD59, and providing treatment to the subject pregnant with the infant subject to reduce, reverse and/or prevent the development of one or more GDM-related conditions in the infant subject. GDM-related conditions may include one or more selected from the group consisting of macrosomia, birth trauma, hyperbilirubinemia, hypoglycemia, seizures and still birth. Gestational windows according to such methods may comprise from about 12 to about 36 weeks of pregnancy. In some cases, treatment may be selected from the group consisting of insulin therapy and diet modification.

BRIEF DESCRIPTION OF THE FIGURES

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

DETAILED DESCRIPTION

Overview

Figure 1:
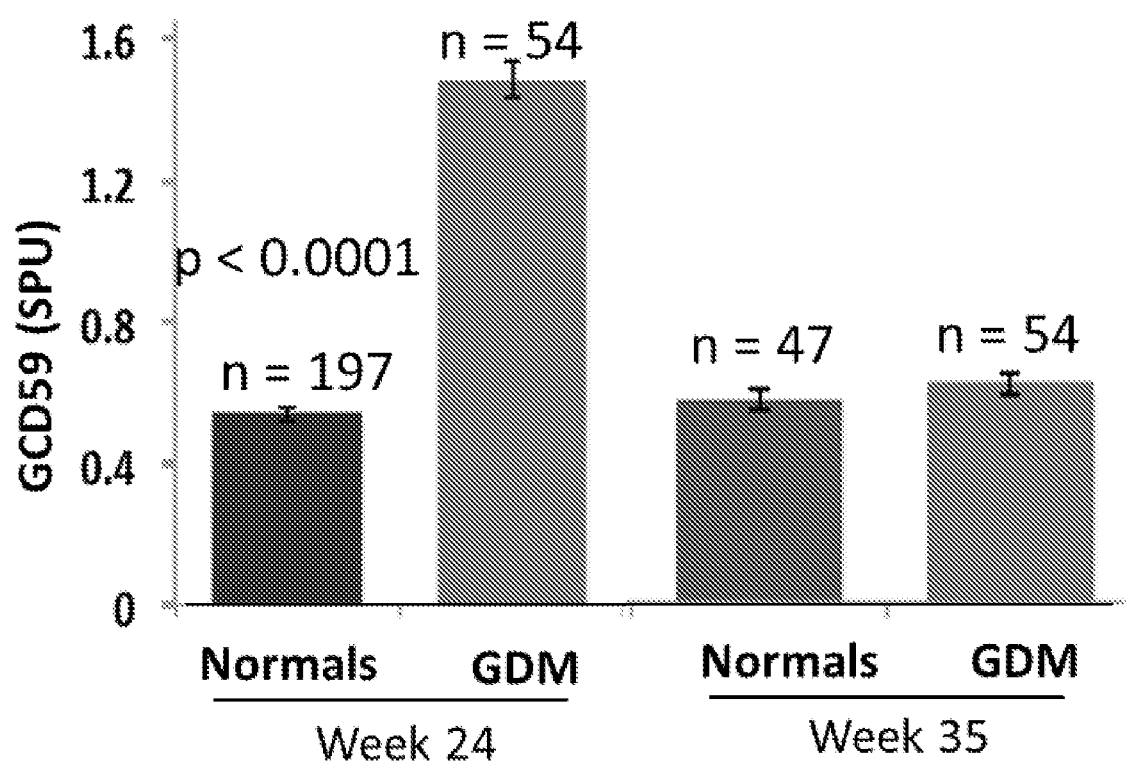
FIG. 1 depicts a graph showing glycated CD59 (GCD59) levels in subject samples obtained from predictors of pre-eclampsia (POP) study cohorts at 24 and 35 weeks of pregnancy.

The discovery that CD59 is glycated facilitates analysis of diseases in which the amount of GCD59 differs from normal levels. For example, it has been discovered that the level of glycation of CD59 is elevated in diabetes (Qin, X. et al., Diabetes. 2004 October 53:2653-61). It also has been determined that GCD59 is present in body fluids. Thus, onset, progression and/or regression of diabetes or other diseases affecting CD59 glycation can be monitored by monitoring levels of GCD59 in bodily fluid samples in subjects.

Embodiments of the present invention utilize levels of glycated proteins, such as the GPI-anchored membrane protein known as CD59, as a stable indicator of diabetic conditions. As used herein, CD59 (also known as membrane inhibitor of reactive lysis (MIRL), protectin, HRF20 and H19) and K41-glycated CD59 are polypeptides as may be translated from the mRNA disclosed by Accession No. M95708 (Davies, A., et al., Journal J Exp. Med. 170 (3), 637-654 (1989)). CD59 is a key regulator of the complement system and is involved in the pathogenesis of the vascular complications associated with diabetes. Under hyperglycemic conditions, glycation of CD59 is increased, particularly at residue K41. As used herein, "K41-glycated CD59" or "GCD59" refers to CD59 which has been glycated at amino acid number 41 of human CD59 (wherein residue number 41 is counted from the mature CD59 protein, obtained after removal of the signal and GPI signal sequences: LQCYN-CPNPTADCKTAVNCS SDFDACLITKAGLQVYNKC-WKFEHCNFNDVTTRLRENE LTYYCCKKDLCNFN-EQLEN (SEQ ID NO:1)). Relative to HbA1c, the establishment of steady state levels of K41 glycated CD59 (GCD59) in blood may allow for shorter intervals between consecutive measurements, providing a much needed intermediate estimate of glycemic status and less burden on subjects undergoing testing (Qin, X. et al., Diabetes. 2004 October 53:2653-61).

In some embodiments, the present invention provides kits, methods and compositions for detecting and measuring K41-glycated CD59 (GCD59) levels, in some cases as they relate to glycemic levels and gestational diabetes mellitus (GDM).

Glycated CD59

Glycation involves the non-enzymatic reaction of reducing sugars (e.g., glucose) with amino groups in proteins, lipids, or other molecules. The glycating sugar may be bound in either a linear or cyclic form. For example, in glycated CD59, the glycating sugar is bound to CD59 in either a linear or cyclic form, and includes the initial aldimine adduct known as the Schiffs base, the cyclized glycosylamine, tautomers of the initial Schiffs base, and the linear (keto) and cyclic (1-deoxy-fructopyranose) forms of the Amadori adduct. Glycated products of CD59 and peptide fragments thereof are described in U.S. Pat. Nos. 6,835,545; 7,049,082; and 7,439,330; the entire contents of each of which are incorporated herein by reference.

In contrast, glycosylation involves the enzymatic attachment of sugars to proteins, lipids, or other molecules. Examples of glycated proteins include those having a glycated α-amino group at the N-terminus (for example, glycated hemoglobin) and those in which the ε-amino group of lysine of a protein has been glycated (for example, glycated albumin). Those proteins, which bear one or more α-amino and/or ε-amino groups that can react preferentially and non-enzymatically with glucose, are appreciated by those skilled in the art as having a glycation motif.

Glycation of proteins is believed to represent the major mechanism by which high levels of glucose over time induce cellular and tissue damage in the target organs of diabetic subjects. Glycation of proteins depends on the glucose levels to which proteins are exposed. Because plasma glucose levels exist as a continuum, it is not surprising that glycated proteins are present in both non-diabetic and diabetic subjects, albeit at higher levels in diabetic subjects than in non-diabetic subjects. Thus, diagnosing and following a diabetic condition in a subject and screening a population of subjects for a diabetic condition can be achieved by detecting the level of glycated proteins, including, but not limited to GCD59, in subjects and/or subject populations.

In some embodiments, subject samples comprise GCD59 comprising glycated lysine residues, wherein glycated side chains of such residues comprise different arrangements of chemical bonds and stereochemical structures. Lysine glycation occurs via the non-enzymatic attachment of glucose or other reducing sugar residues to the amino group of a lysine residue side chain. When glucose first reacts with the lysine side chain, it forms a Schiff base or aldimine with the ε-amino group. This labile Schiff's base can cyclize to form a more stable glycosylamine or rearrange and cyclize to Amadori adducts as shown below.

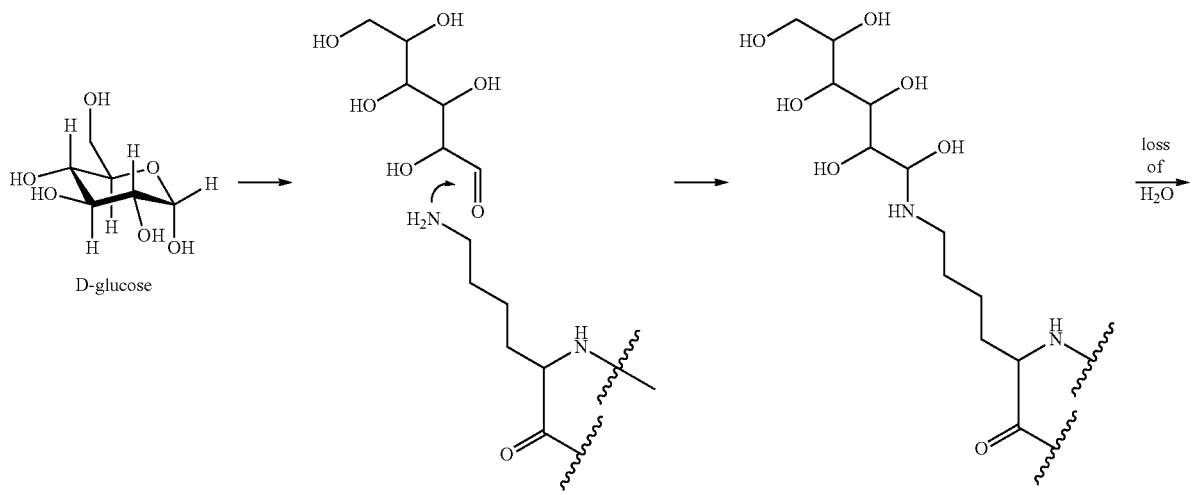

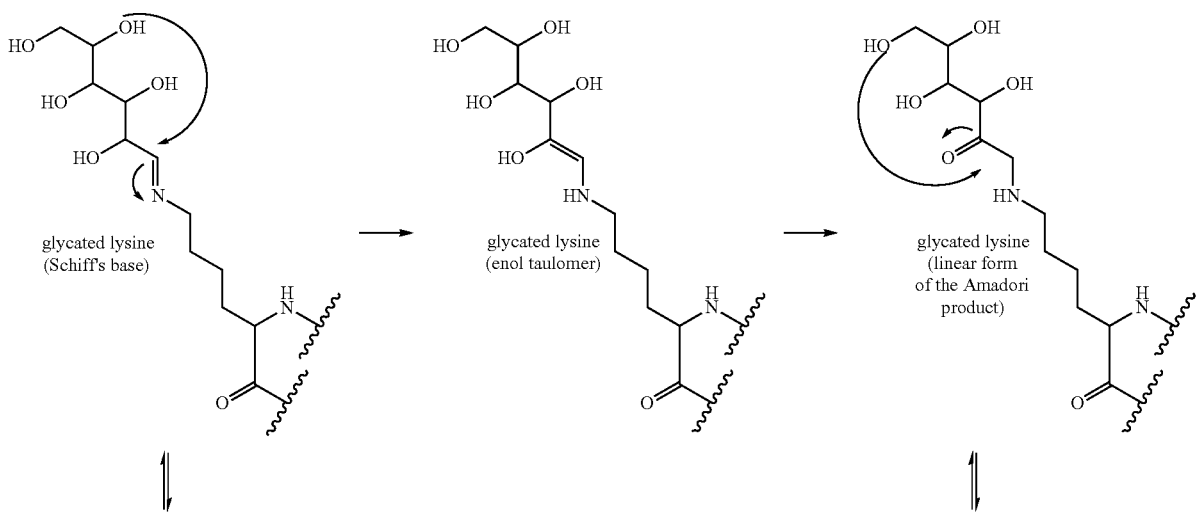

-continued

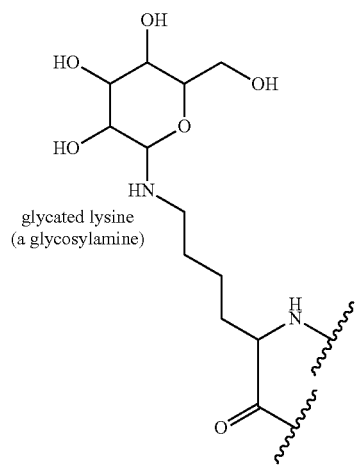

glycated lysine
(a glycosylamine)

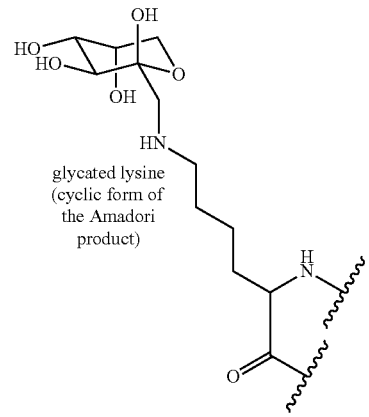

glycated lysine
(cyclic form of
the Amadori
product)

It has been determined, previously, that excessive/abnormal K41-glycation of CD59 Ccorrelates with abnormal blood sugar levels and that glycation at K41 interferes with the normal activity of CD59. CD59 functions normally by binding to the terminal components of the membrane attack complex (MAC) of complement, thereby interfering with membrane insertion and polymerization of the C9 component of complement. Glycation at the K41 residue of CD59 interferes with CD59's ability to prevent the assembly of the MAC. It is believed that, as a result of K41-glycation of CD59, there is no inhibition of MAC pore formation, which leads to the development of proliferative chronic diabetic complications (see U.S. Pat. Nos. 6,835,545, 7,049,082, 7,767,791, 8,008,024, 8,298,779 and 7,439,330, the contents of each of which are incorporated herein by reference in their entirety).

GCD59 Detection Kit

In some embodiments, the present invention provides a kit for the detection of GCD59. Such kits may detect and quantify GCD59 in subject samples. As used herein, the term "subject sample" refers to a sample from a subject. Subject samples may comprise bodily fluids. Such bodily fluid subject samples may include, but are not limited to blood, urine, mucous, amniotic fluid, plasma, ascites, cerebrospinal fluid, sputum, bone marrow, synovial fluid, aqueous humor, breast milk, sweat, fecal matter, tears, peritoneal fluid, lymph, vaginal secretions, blastocyl cavity fluid, umbilical cord blood and/or saliva.

In some embodiments, kits of the present invention may comprise immunological assays. As used herein, the term "immunological assay" refers to any assay comprising the use of antibodies for one or more means of detection and/or measurement. Immunological assays (e.g. enzyme-linked immunosorbent assay (ELISA)) may comprise "sandwich assays." As used herein, the term "sandwich assay" refers to an immunological assay wherein factors being detected are bound by at least two antibodies, wherein one antibody captures such factors and another antibody associates only with regions, features or epitopes of such factors with which detection is desired. Such assays typically comprise a capture antibody and a detection antibody. As used herein, the term "capture antibody" refers to an antibody component of an immunological assay, typically bound to a substrate, capable of associating with an antigen or other factor being detected in an assay. Capture antibodies may bind to one or more capture epitope. When referring to factors being detected in a sandwich assay, the term "capture epitope," as used herein, refers to an epitope that does not comprise regions, features or epitopes of such factors that bind to detection antibodies in such sandwich assays. Association of capture antibodies with one or more capture epitopes holds factors being detected in an orientation that facilitates interaction of such factors with a detection antibody.

As used herein, the term "detection antibody" refers to an antibody component of an immunological assay that associates with one or more detection epitopes. When referring to factors being detected in a sandwich assay, the term "detection epitope" refers to an epitope that comprises regions, features or epitopes of such factors that are being detected in such sandwich assays. Detection antibodies may be associated with one or more detectable labels to facilitate detection and/or quantification of bound antigens. Such labels may include, but are not limited to fluorescent tags, biotin moieties and/or enzymes. Detectable labels comprising enzymes may comprise horseradish peroxidase (HRP).

In some embodiments, sandwich assays of the present invention may comprise secondary detection antibodies. As used herein, the term "secondary detection antibody" refers to an antibody capable of associating with detection antibodies. Secondary detection antibodies may comprise detectable labels. Such labels may include, but are not limited to fluorescent tags, biotin moieties and/or enzymes. Some detectable labels comprising enzymes may comprise HRP.

In some embodiments, kits may include reagents and/or instructions for use. Such kits may include one or more buffers. These may include, but are not limited to citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

In some embodiments, kit components may be packaged either in aqueous media or in lyophilized form. The container means of the kits will generally include at least one vial, test tube, flask, bottle, syringe or other container means, into which a component may be placed, and preferably, suitably aliquoted. Where there are more than one kit component, (labeling reagent and label may be packaged together), kits may also generally contain second, third or other additional containers into which additional components may be separately placed. Some kits may also comprise second container means for containing sterile, pharmaceutically acceptable buffers and/or other diluents.

In some embodiments, various combinations of components may be comprised in one or more vial. Kits of the present invention may also include means for containing compounds and/or compositions of the present invention, e.g., proteins, nucleic acids, and any other reagent containers in close confinement for commercial sale. Such containers may include injection or blow-molded plastic containers into which desired vials are retained.

Kit components may be provided in one and/or more liquid solutions. Such liquid solutions may be aqueous solutions, including, but not limited to sterile aqueous solutions. Some kit components may be provided as dried powder(s). When reagents and/or components are provided as dry powders, such powders may be reconstituted by the addition of suitable volumes of solvent. Solvents may be provided in another container means or may be required to be supplied by an individual utilizing such kits. Some kits may include instructions for employing kit components as well as the use of any other reagent not included in the kit. Instructions may include variations that may be implemented.

In some embodiments, kits of the present invention may comprise sandwich assays for detection and/or quantitation of GCD59, referred to herein as GCD59 detection and/or quantitation assays. In some cases, such assays may comprise any of those described in Ghosh et al. (Ghosh et al., 2013. Am. J. Hematol. 88:670-6, the contents of which are herein incorporated by reference in their entirety).

Antibodies, Antigens and Assays

GCD59 detection and/or quantitation assays of the present invention may comprise one or more capture antibody, one or more detection antibody, one or more secondary detection antibody and/or a protein standard (optionally comprising one or more surrogate compounds). As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies are primarily amino-acid based molecules but may also comprise one or more modifications (including, but not limited to the addition of one or more detectable labels). Capture antibodies of GCD59 detection and/or quantitation assays disclosed herein may be capable of associating with CD59. Such capture antibodies may associate with one or more capture epitopes present on CD59. In GCD59 detection and/or quantitation assays, capture epitopes present on CD59 may or may not comprise the K41 residue.

In some embodiments, capture epitopes may be selected from the mature CD59 protein (without an N-terminal secretion- and GPI-signal sequences, SEQ ID NO: 1). Some capture epitopes present on CD59 may comprise the amino acid sequence FEHCNFNDVTTRLRENELTYYCCKKDL (SEQ ID NO:2). Some capture epitopes present on CD59 may comprise the amino acid sequence FEHCNFNDVT-TRLRENELTYYCCKK (SEQ ID NO:3). Some capture epitopes present on CD59 may comprise the amino acid sequence HCNFNDVTTRLRENELTYYCCKK (SEQ ID NO:4).

In some embodiments, capture antibodies of the present invention may be produced by using peptide antigens. As used herein, the terms "peptide antigen" and "protein antigen" refer to peptides and/or proteins that may be used to elicit an immune response in one or more hosts in order to generate antibodies that specifically associate with such peptides and/or proteins. Peptide antigens corresponding to capture epitopes on CD59 and/or peptide antigens with partial identity to such peptides may be used to produce capture antibodies.

According to this method, capture antibodies may be produced that specifically associate with peptide antigens used. Peptide antigens comprising amino acid sequences of any of SEQ ID NOs:2-4 or derivatives thereof may be used to produce capture antibodies. Peptide antigens corresponding to CD59 may be modified and/or mutated before being used to produce capture antibodies. Such modifications may comprise incorporation of non-coded amino acids. Such modifications and/or mutations may enable proper folding of such peptide antigens. Some modifications and/or mutations may increase stability of such peptide antigens and/or ensure desired folding. Peptide antigens comprising SEQ ID NO:4 may be mutated to comprise the amino acid sequence ACNFNDVTTRLRENELTYYCAAK (SEQ ID NO:5) and used to produce capture antibodies.

In some embodiments, peptide antigens comprising SEQ ID NO:2 may be mutated and used to produce capture antibodies. Peptide antigens comprising SEQ ID NO:2 may comprise non-coded amino acids. The 20 coded proteinogenic amino acids are identified and referred to herein by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala: A), arginine (Arg:R), cysteine (Cys:C), tryptophan (Trp:W), valine (Val:V), glutamine (Gln:Q) methionine (Met:M), asparagine (Asn:N). In nature, coded amino acids exist in their levorotary (L) stereoisomeric forms. Amino acids referred to herein are L-stereoisomers except where otherwise indicated. As used herein, the term "non-coded amino acid" refers to amino acids having side chains or other features not present in the 20 coded amino acids listed above and may include, but are not limited to: N-methyl amino acids, N-alkyl amino acids, alpha, alpha-disubstituted amino acids, beta-amino acids, D-amino acids, and other non-coded amino acids known in the art (See, US Patent Application Publication No. 2011/0172126, the contents of which are herein incorporated by reference in their entirety). Further examples of non-coded amino acids include, but are not limited to β-alanine (βA) and alpha-amino-isobutyric acid (Aib).

In some embodiments, peptide antigens comprising AFE-HCNFNDVTTRLRENELTYYCAAKDL (SEQ ID NO:6) may be used to produce capture antibodies or may be mutated to comprise non-coded amino acids (e.g. βA and/or Aib) before being used to produce capture antibodies. Such mutated peptide antigens may comprise the amino acid sequence AFEHCNFNDVTTRLRENELTYYC(βA)KDL (SEQ ID NO:7) and/or AFEHCNFNDVTTRLRENELTYY-C(Aib)AKDL (SEQ ID NO:8).

In some embodiments, peptide antigens used to produce capture antibodies may comprise disulfide bonds between cysteine residues comprised in such peptide antigens. Some peptide antigens comprising disulfide bonds may be cyclic and/or comprise cyclic loops or loop structures. Peptide antigens comprising the amino acid sequence of SEQ ID NOs: 4 or 5 comprise a disulfide bond between C2 and C20 (which correspond to residues 39 and 63 in the mature CD59 sequence) resulting in the presence of a cyclic loop in such antigens. Peptide antigens comprising the amino acid sequence of SEQ ID NOs: 6-8 may comprise a disulfide bond between C5 and C23 (which correspond to residues 39 and 63 in the mature CD59 sequence) also resulting in cyclic loop structures in such antigens.

In some embodiments, detection antibodies of GCD59 detection and/or quantitation assays disclosed herein may be capable of associating with detection epitopes present on CD59. In GCD59 detection and/or quantitation assays, detection epitopes present on CD59 may or may not comprise glycated K41, also referred to herein as "K*41" or "K*" when listed as part of a sequence.

In some embodiments, detection epitopes may be selected from the mature CD59 protein (without an N-terminal secretion- and GPI-signal sequences, SEQ ID NO: 1). Such detection epitopes present on CD59 may comprise the amino acid sequence NKCWKFEHCNFNDV (SEQ ID NO:9).

Detection epitopes may also comprise one or more glycated lysine residue. Glycated residues may comprise different arrangements of chemical bonds and stereochemical structures. Some glycated lysine residues of detection epitopes may comprise any of the structures formed during lysine glycation and/or rearrangement, including any intermediate forms. This includes any of the structures I-VI.

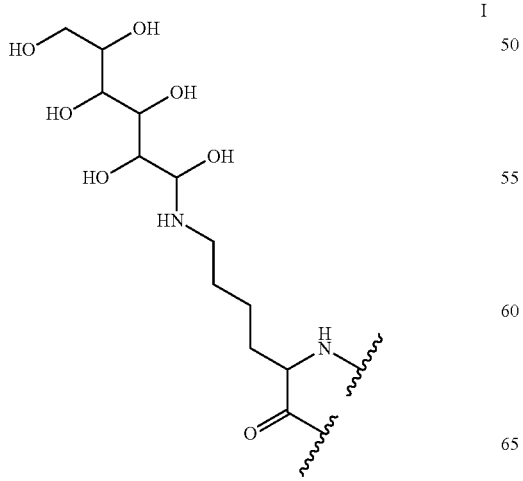

I

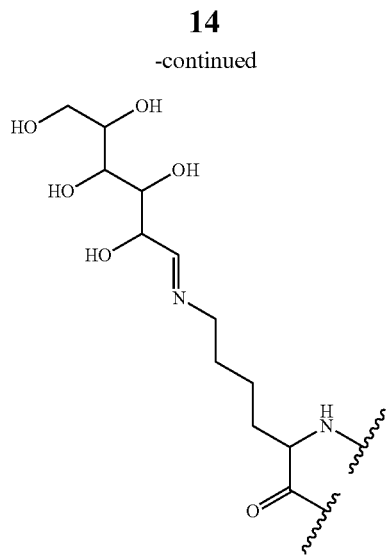

II

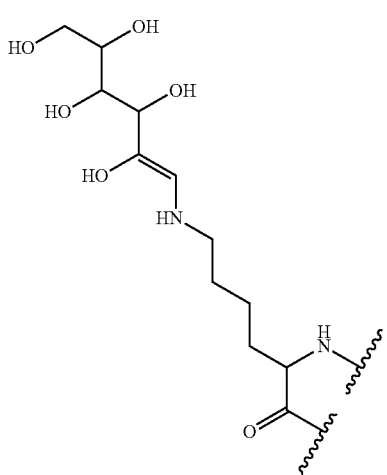

III

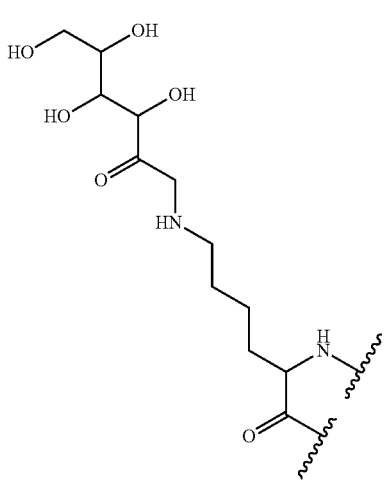

IV

-continued

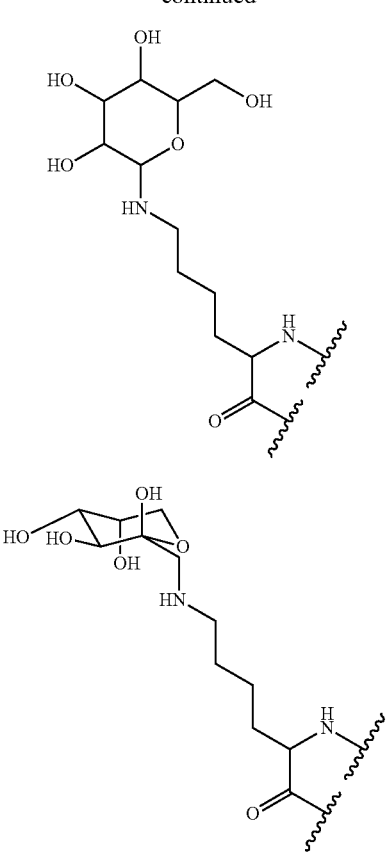

V

VI

In some embodiments, glycated lysine residues of detection epitopes may comprise Amadori products. Such Amadori products present on detection epitopes may be in linear or cyclic form. Some detection epitopes may comprise glycated lysine residues wherein glycated side chains have been reduced as in glucitollysine (pictured below as structure VII).

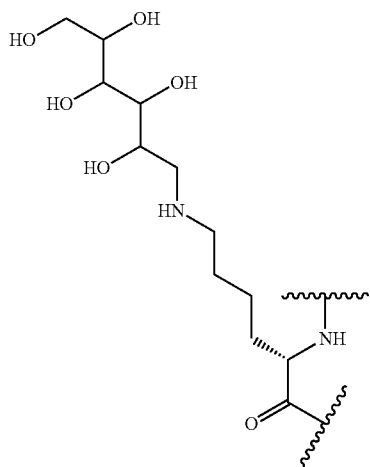

VII

In some embodiments, glycated lysine residues may be reduced through chemical reaction with one or more reducing agents. Such treatments may induce glycated lysine residues to adopt the conformation of glucitollysine. Such reducing agents may include, but are not limited to sodium cyanoborohydride ($NaCNBH_3$) for reduction of glycated lysine residues comprising Schiff's bases and/or sodium borohydride ($NaBH_4$) for reduction of both glycated lysine residues comprising Schiff's bases and residues comprising Amadori products.

Detection antibodies of the present invention may be produced by using peptide and/or protein antigens to elicit an immune response in one or more hosts. Peptide antigens corresponding to detection epitopes on GCD59 and/or peptide antigens with partial identity to such peptides may also be used to produce detection antibodies. According to this method, detection antibodies may be produced that specifically associate with peptide antigens used. Peptide antigens comprising the amino acid sequence of SEQ ID NO:9 may be used to produce detection antibodies.

In some embodiments, peptide antigens corresponding to GCD59 may be modified and/or mutated before being used to produce detection antibodies. Such modifications may comprise incorporation of non-coded amino acids. In some cases, such modifications and/or mutations may ensure desired folding of such peptide antigens or modulate the stability of such peptide antigens. Mutated peptide antigens may comprise SEQ ID NO:9 mutated to comprise the amino acid sequence NKAWKFEHANFND (SEQ ID NO: 10). Such peptide antigens may be used to produce detection antibodies. Some peptide antigens comprising SEQ ID NOs: 9 and/or 10 may comprise a glycated K5 residue (corresponding to K41 of the mature CD59 protein (SEQ ID NO: 1)). Such glycated lysine residues of such peptide antigens may comprise any of the structures formed during lysine glycation and/or rearrangement and/or reduction, including any intermediate forms. This includes any of the structures I-VII.

Some peptides of the present invention may comprise end-group modifications. Such end-group modifications may include N-terminal acetylation, indicated herein by "Ac-." C-terminal residues may comprise carboxamide groups, indicated herein by "—$NH_2$."

In some embodiments, antibodies, antibody fragments, their variants or derivatives as described above are specifically immunoreactive with antigenic proteins, peptides, epitopes and/or domains as described herein. Antibodies and/or antigens of the present invention may include any of those disclosed by Ghosh et al. (Ghosh et al., 2013. Am. J. Hematol. 88:670-6, the contents of which are herein incorporated by reference in their entirety).

In some cases, antigens may be conjugated to or synthesized as a fusion protein with one or more antigen carriers prior to use as an immunogen. As used herein, the term "antigen carrier" refers to a protein, protein complex of other macromolecular structure that may be conjugated to one or more antigen to decrease particulate and/or gel formation upon immunization. Further, antigen carriers may increase antigen stability before, during and/or after immunization. Antigen carriers that may be used herein may include, but are not limited to keyhole limpet hemocyanin (KLH), serum albumin, bovine thyroglobulin, soybean trypsin inhibitor, multiple antigenic peptide systems and the like. In some embodiments, antigens of the present invention may be conjugated to KLH (see U.S. Pat. No. 5,855,919, the contents of which are herein incorporated by reference in their entirety). KLH comprises a large number of lysine residues that facilitate antigen coupling and enable a large ratio of antigen to antigen carrier to promote an antigen-specific immune reaction.

As used herein the term, "antibody fragment" refers to any portion of an intact antibody. In some embodiments, antibody fragments comprise antigen binding regions from intact antibodies. Examples of antibody fragments may include, but are not limited to Fab, Fab', F(ab')$_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')2 fragment that has two antigen-binding sites and is still capable of cross-linking antigens. Kits of the present invention may comprise one or more of these fragments. For the purposes herein, antibodies may comprise a heavy and light variable domains as well as an Fc region.

As used herein, the term "native antibody" refers to a usually heterotetrameric glycoprotein of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains that differ extensively in sequence among antibodies and are responsible for binding and specificity of each particular antibody for its particular antigen.

As used herein, the term "Fv" refers to antibody fragments comprising complete antigen-recognition and antigen-binding sites. These regions consist of a dimer of one heavy chain and one light chain variable domain in tight, non-covalent association.

As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. As used herein, the term "Single-chain Fv" or "scFv" refers to a fusion protein of $V_H$ and $V_L$ antibody domains, wherein these domains are linked together into a single polypeptide chain. Fv polypeptide linkers may enable scFvs to form desired structures for antigen binding.

As used herein, the term "diabody" refers to a small antibody fragment with two antigen-binding sites. Diabodies comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (Hollinger, P. et al., PNAS. 1993. 90:6444-8) the contents of each of which are incorporated herein by reference in their entirety.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method.

In some cases, monoclonal antibodies may be rabbit monoclonal antibodies. Such antibodies may be produced, for example, according to any of the methods taught in U.S. Pat. Nos. 5,675,063, 7,429,487, 7,732,168, 8,062,867 or 8,367,408 or US Publication Numbers 2011/0020934 or 2014/0004566, the contents of each of which are herein incorporated by reference in their entirety. Such methods may include the use of rabbit plasmacytoma cells, rabbit fusion partner cells and/or rabbit hybridoma cells. Rabbit plasmacytoma cells may include, but are not limited to 240E1-1 cells, as described in U.S. Pat. No. 5,675,063 and corresponding to ATCC Accession No. CRL-11872. Rabbit fusion partner cells may express oncogenes (e.g., myc and/or abl oncogenes) and may include, but are not limited to 240E1-1-2 cells as described in U.S. Pat. No. 5,675,063 and corresponding to ATCC Acession No. HB11870. In some cases, rabbit hybridomas may include those of ATCC Accession No. HB-11871, also described in U.S. Pat. No. 5,675,063.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity.

As used herein, the term "hypervariable region" refers to regions within the antigen binding domain of an antibody comprising amino acid residues responsible for antigen binding. The amino acids present within the hypervariable regions determine the structure of the complementarity determining region (CDR). As used herein, the term "CDR" refers to regions of antibodies comprising a structure that is complimentary to its target antigen or epitope.

In some embodiments, compounds and/or compositions of the present invention may be antibody mimetics. As used herein, the term "antibody mimetic" refers to any molecule which mimics the function or effect of an antibody and which binds specifically and with high affinity to their molecular targets. Some antibody mimetics may be monobodies, designed to incorporate the fibronectin type III domain (Fn3) as a protein scaffold (U.S. Pat. No. 6,673,901; 6,348,584). Antibody mimetics may include any of those known in the art including, but not limited to affibody molecules, affilins, affitins, anticalins, avimers, Centyrins, DARPINS™ Fynomers and Kunitz and domain peptides. In other embodiments, antibody mimetics may include one or more non-peptide region.

As used herein, the term "antibody variant" refers to a biomolecule resembling an antibody in structure and/or function comprising some differences in their amino acid sequence, composition or structure as compared to a native antibody.

The preparation of antibodies, whether monoclonal or polyclonal, is known in the art. Techniques for the production of antibodies are well known in the art and described, e.g., in Harlow and Lane, Cold Spring Harbor Laboratory Press, 1988 and Harlow and Lane, Cold Spring Harbor Laboratory Press, 1999. The production of monoclonal antibodies may comprise host immunization with one or more antigens comprising one or more proteins, peptides or other molecules to elicit lymphocytes that specifically bind such antigens. Lymphocytes are collected and fused with an immortalized cell line. The resulting hybridoma cells are cultured in a suitable culture medium with a selection agent to support the growth of only the fused cells.

In some cases, antibodies of the present invention may also be made by recombinant methods, such as those described in U.S. Pat. No. 4,816,567, US Publication No. 2004/0067496, or International Publication Nos. WO2014/004586A1, or WO2004/032841, the contents of each of which are herein incorporated by reference in their entirety. Nucleic acid (e.g., DNA, RNA, cDNA) sequences encoding antibodies of the invention may be readily obtained through isolation, amplification and/or sequencing using conventional procedures. For example, nucleic acids encoding heavy and light chains of a desired antibody may be amplified by polymerase technologies (e.g., PCR, RT-PCR) using oligonucleotide probes that are capable of binding specifically to such nucleic acids (Orlandi et al., Proc. Natl. Acad. Sci. USA 86 (1989) 3833-7, the contents of which are herein incorporated by reference in their entirety). In some cases, hybridoma cells may serve as a preferred source of nucleic acid. Once isolated or otherwise obtained, nucleic acids may be placed into expression vectors. Expression vectors may then be transfected into host cells for antibody expression. Host cells may include, but are not limited to simian COS cells, Chinese hamster ovary (CHO) cells, VERO cells, HeLa cells, HEK293 cells, NSO cells, W138 cells, BHK cells, COS-7 cells, Caco-2 cells, MDCK cells and myeloma cells (and subclasses and variants thereof). In some cases, such host cells do not otherwise produce immunoglobulin protein. Antibodies of the present invention may also be obtained by modifying nucleic acids encoding known antibodies such that coding sequences for human heavy and light chain constant domains are used to replace homologous sequences from other species (see, U.S. Pat. No. 4,816,567 or 7,462,697, International Publication Nos. WO2004/016740 or WO2005/016950, or European Publication Nos. EP1651659 or EP1539947, the contents of each of which are herein incorporated by reference in their entirety) that may be present in such nucleic acids.

Antibodies of the present invention may also be developed through optimization of one or more known antibodies. Such optimization may comprise alteration of one or more desired properties. Methods of optimizing antibodies can be found, for example, in Strohl, W R and Strohl L M, "Therapeutic Antibody Engineering," Cambridge: Woodhead Publishing (2012), Chapter 6, the contents of which are herein incorporated by reference in their entirety. In some cases, antibodies may be optimized to modulate affinity for their binding partners. Such optimization may comprise alteration of antibody amino acid sequences by addition, deletion or substitution of one or more amino acids. In some cases, antibodies may be optimized according to any of the methods described in U.S. Pat. No. 8,404,816, International Publication No. WO2006/050491 or European Patent No. EP1819830, the contents of each of which are herein incorporated by reference in their entirety.

Alterations that modulate antibody affinity may be made, in some cases, to antibody CDR regions. Antibody affinity for binding partners may be assessed according to methods known in the art including, but not limited to ELISA, Surface Plasmon Resonance (SPR) and kinetic exclusion assay technology.

Protein Standards

Kits of the present invention comprise one or more protein standards. As used herein, the term "protein standard" refers to a component of immunological assays used for calibration and to enable accurate quantification of one or more factors being assessed by such assays. Protein standards may comprise known concentrations of one or more factors being analyzed by an immunological assay. Some protein standards may comprise variants of such factors. Some protein standards of the current invention may comprise surrogate compounds comprising synthetic constructs that act as surrogates of one or more proteins being quantified. As used herein, the term "surrogate compound," refers to an entity that takes the place of another entity in certain contexts. Some surrogate compounds of the present invention are designed to be used as protein standards, replacing CD59 or variants thereof in protein standard preparations. Such surrogate compounds may comprise two or more amino acid sequences taken from the mature CD59 protein (SEQ ID NO:1). Such surrogate compound amino acid sequences may comprise one or more capture domains. As used herein, the term "capture domain" refers to a protein domain that associates with one or more capture antibody. Surrogate compounds of the present invention may also comprise one or more detection domains. As used herein, the term "detection domain" refers to a protein domain that associates with one or more detection antibody.

Surrogate compounds of the present invention may comprise capture domains comprising any of the capture epitopes described herein and/or any of the peptide antigens described herein that correspond with any of the capture epitopes described herein. Some capture domains may comprise one or more amino acid sequences of SEQ ID NOs:2-8.

In some embodiments, surrogate compounds of the present invention may comprise detection domains comprising any of the detection epitopes described herein and/or any of the peptide antigens described herein that correspond with any of the detection epitopes described herein. Some detection domains may comprise one or more of the amino acid sequences of SEQ ID NOs: 9 or 10. Some detection domains may comprise glycated lysine residues. Such glycated lysine residues of detection domains may comprise any of the structures formed during lysine glycation and/or rearrangement, including any intermediate forms. These may include any of the structures I-VI including the reduced structure VII.

In some embodiments, surrogate compounds of the present invention may comprise any of the surrogate compounds disclosed in International Patent Application number PCT/US2012/024645, entitled Surrogates of Post-Translationally Modified Proteins and Uses Thereof, the contents of which are herein incorporated by reference in their entirety.

Glycated lysine residues present on detection domains may comprise Amadori products. Such Amadori products present on detection domains may be in linear or cyclic form. Some detection domains may comprise glucitollysine.

In some embodiments, capture domains and detection domains of surrogate compounds of the present invention are joined by a linker. As used herein, the term "linker" refers to a compound or molecule used to link to proteins, peptides, domains or moieties. Linkers may be independently cyclic or acyclic, substituted or unsubstituted, branched or unbranched heteroaliphatic moieties. In further embodiments, linkers may be from about 1 to about 500 atoms in length. In still further embodiments, linkers may comprise polymeric regions. Such polymeric regions may comprise from about 1 to about 100 monomers. In further embodiments, polymeric regions may comprise from about 10 to about 60 monomers. In still further embodiments, polymeric regions may comprise from about 20 to about 40 monomers. Some polymeric regions may comprise ethylene glycol monomers. In further embodiments, polymeric regions may comprise propylene glycol monomers. In still further embodiments, linkers may not comprise a charge.

In some embodiments, linkers of the present invention may comprise a structure according to VIII:

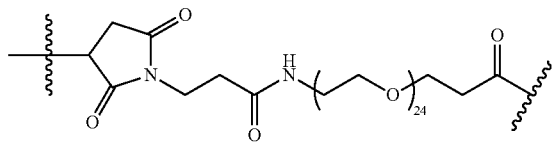

VIII

In some embodiments, linkers of the present invention may comprise a structure according to IX:

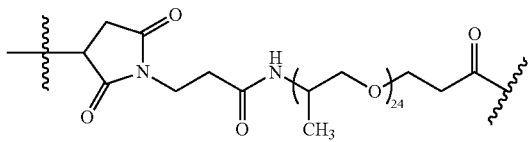

IX

Protein standards described herein may be assayed along with subject samples in order to determine concentrations of one or more factors being assayed. Some protein standards described herein are assayed along with subject samples to enable the determination of GCD59 concentration in such samples. In some cases, concentrations of GCD59 comprising alternative forms of glycated lysine are determined. Some assays of the present invention may comprise the preparation of various solutions with known concentrations of protein standards in each. These solutions may be assayed along with subject samples and used to generate standard curves by plotting the known concentration in each protein standard solution against one or more signals produced by the assay. Standard curves are then compared against signals produced from subject sample analysis and used to extrapolate concentration values for the one or more factors being analyzed.

In some embodiments, protein standards of the present invention may comprise any of the surrogate compounds disclosed in International application number PCT/US2012/024645, the contents of which are herein incorporated by reference in their entirety. Methods of synthesis for such surrogate compounds may comprise any of those disclosed for the surrogate compounds disclosed in International application number PCT/US2012/024645 as well.

Variations

Any of the proteins disclosed herein (including, but not limited to antibodies, fusion proteins, surrogate compounds, peptides and/or peptide antigens) may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, the term "polypeptide" refers to a polymer of amino acid residues (natural or non-coded) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

As used herein, the term "variant," when referring to a protein or peptide, refers to molecules which differ in their amino acid sequence from a native or reference sequence. The amino acid sequence variants may possess substitutions, deletions, and/or insertions at certain positions within the amino acid sequence, as compared to a native or reference sequence. Peptide variants may comprise one or more non-coded amino acid. Some peptides, polypeptides and/or fragments thereof may comprise both naturally and non-coded amino acids and/or modified amino acids or be exclusively comprised of non-coding amino acids. Non-coded amino acids may include, but are not limited to β-alanine and α-amino isobutyric acid.

Ordinarily, variants will possess from about 50% identity (homology) to about 99% identity to a native or reference sequence. Some variants may comprise from about 50% to about 75% identity, from about 60% to about 85% identity, from about 70% to about 95% identity or from about 80% to about 99% identity to a native or reference sequence.

As used herein, the terms "native" or "starting" when referring to sequences are relative terms referring to an original molecule against which a comparison may be made. Native or starting sequences should not be confused with wild-type sequences. Native sequences or molecules may represent the wild-type (that sequence found in nature) but do not have to be identical to the wild-type sequence.

As used herein, the term "homolog" as it applies to amino acid sequences is meant the corresponding sequence of other species having substantial identity to a second sequence of a second species.

As used herein, the term "analog" is meant to include polypeptide variants which differ by one or more amino acid alterations, e.g., substitutions, additions or deletions of amino acid residues that still maintain the properties of the parent polypeptide.

As used herein, the term "derivative" is used synonymously with the term "variant" and refers to a molecule that has been modified or changed in any way relative to a reference molecule or starting molecule.

Detectable labels and/or amino acids, such as one or more lysines, can be added to peptide sequences of the invention (e.g., at the N-terminal or C-terminal ends). Detectable labels may be used for peptide purification or localization. Lysines may be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein, the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

As used herein, the term "insertional variants" when referring to proteins are those with one or more amino acids inserted immediately adjacent to an amino acid at a particular position in a native or starting sequence. As used herein, the term "immediately adjacent" refers to an adjacent amino acid that is connected to either the alpha-carboxy or alpha-amino functional group of a starting or reference amino acid.

As used herein, the term "deletional variants" when referring to proteins, are those with one or more amino acids in the native or starting amino acid sequence removed. Ordinarily, deletional variants will have one or more amino acids deleted in a particular region of the molecule.

As used herein, the term "derivatives," as referred to herein includes variants of a native or starting protein comprising one or more modifications with organic proteinaceous or non-proteinaceous derivatizing agents, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

As used herein, the term "features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein, the term "fold", when referring to proteins, refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein, the term "turn" as it relates to protein conformation, refers to a bend which alters the direction of the backbone of a peptide or polypeptide and may involve one, two, three or more amino acid residues.

As used herein, the term "loop" when referring to proteins, refers to a structural feature of a peptide or polypeptide which reverses the direction of the backbone of a peptide or polypeptide and comprises four or more amino acid residues. Oliva et al. have identified at least 5 classes of protein loops (Oliva, B. et al., 1997. 266(4):814-30).

As used herein, the term "half-loop" when referring to proteins, refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein, the term "domain," when referring to proteins, refers to a motif of a protein or peptide having one or more identifiable structural or functional characteristics or properties (e.g., comprising a glycated residue, ability to associate with one or more factors, serving as a site for protein-protein interactions).

As used herein, the term "half-domain," when referring to proteins, refers to a portion of an identified domain having at least half the number of amino acid residues as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein, the terms "site," as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein, the terms "termini" or "terminus," when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

In some embodiments, proteins and/or peptides of the present invention may comprise one or more atoms that are isotopes. As used herein, the term "isotope" refers to a chemical element that has one or more additional neutrons. Some polypeptides of the present invention may be deuterated. As used herein, the term "deuterate" refers to the process of replacing one or more hydrogen atoms in a substance with deuterium isotopes. Deuterium isotopes are isotopes of hydrogen. The nucleus of hydrogen contains one proton while deuterium nuclei contain both a proton and a neutron. The polypeptides of the present invention may be deuterated in order to change one or more physical property, such as stability, or to allow for use in diagnostic and/or experimental applications.

Conjugates and Combinations

In some embodiments, polypeptides of the present invention may be complexed, conjugated or combined with one or more homologous or heterologous molecules. As used herein, the term "homologous molecule" refers to a molecule which is similar in at least one of structure or function relative to a starting molecule while a "heterologous molecule" is one that differs in at least one of structure or function relative to a starting molecule. Structural homologs are therefore molecules which may be substantially structurally similar. Such homologs may be identical. Functional homologs are molecules which may be substantially functionally similar. In some cases, such homologs may be identical.

In some embodiments, polypeptides of the present invention may comprise conjugates. Such conjugates of the invention may include naturally occurring substances or ligands, such as proteins (e.g., human serum albumin (HSA), low-density lipoprotein (LDL), high-density lipoprotein (HDL), or globulin); carbohydrates (e.g., a dextran, pullulan, chitin, chitosan, inulin, cyclodextrin or hyaluronic acid); or lipids. Conjugates may also be recombinant or synthetic molecules, such as synthetic polymers, e.g., synthetic polypeptides, polyamino acid conjugates and oligonucleotides (e.g., aptamers). Examples of polyamino acids include, but are not limited to polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazene. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Nucleic Acids

In some embodiments, nucleic acids may encode polypeptides of the present invention. Such nucleic acid molecules may include, without limitation, DNA molecules, RNA molecules, polynucleotides, oligonucleotides, mRNA molecules, vectors, plasmids and the like. The present invention also includes cells, cell lines, hybridomas and the like. Some cell may be programmed or generated to express nucleic acid molecules encoding polypeptides of the present invention.

Samples

In some embodiments, assays of the present invention facilitate the assessment of glycated CD59 levels in subject samples. Subject samples may comprise GCD59 wherein K41 glycated residues comprise glycated side chains comprising varying arrangements of chemical bonds and stereochemical structures. Examples of such glycated side chain structures include I-VI.

Detection of GCD59 in subject samples, wherein GCD59 comprises any of the glycated side chain structures, may be carried out using assays of the present invention. Such assays may comprise detection antibodies capable of recognizing one or more of such GCD59 glycated side chain structures. Such assays may also be carried out without pretreatment of subject samples.

In some embodiments, assays of the present invention may require that subject samples be pretreated with one or more reducing agents prior to GCD59 detection. Treatment of subject samples with reducing agents may reduce one or more glycated side chain structures (see below).

products to glucitollysine. The chemical properties of NaBH$_4$ as well as its uses in organic reductions are well known in the art. Such properties and uses can be found described in detail in Rohm and Haas: The Sodium Borohydride Digest, 2003, pages 1-212, the contents of which are herein incorporated by reference in their entirety.

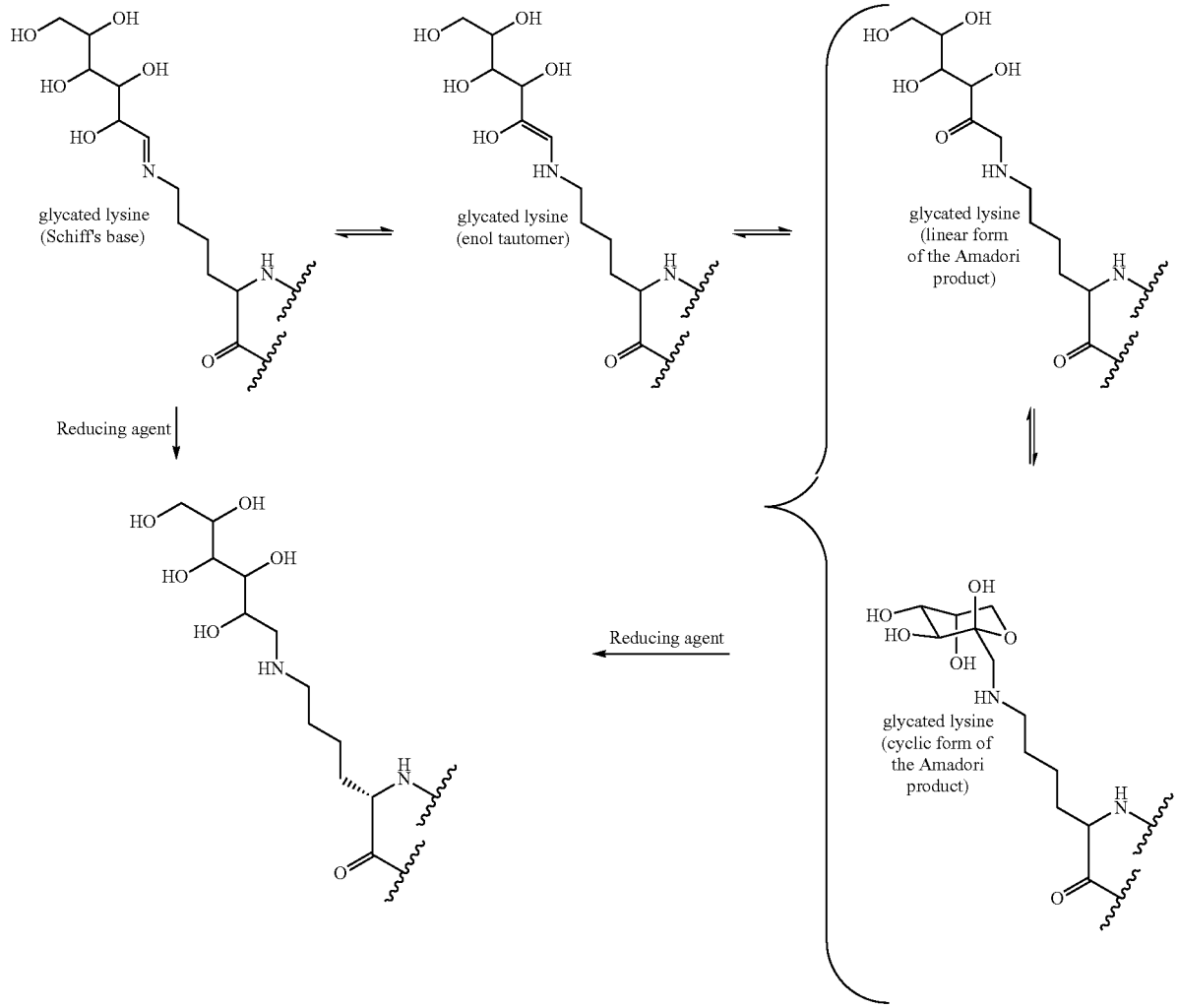 [SMILES: *NC(CCCC/N=C/C(O)C(O)C(O)C(O)CO)C(*)=O ; *NC(CCCCN/C=C(\O)C(O)C(O)C(O)CO)C(*)=O ; *NC(CCCCNCC(=O)C(O)C(O)C(O)CO)C(*)=O ; *N[C@@H](CCCCNCC(O)C(O)C(O)C(O)CO)C(*)=O ; *NC(CCCCNCC1(O)OCC(O)C(O)C1O)C(*)=O]

As used herein, the term "reducing agent" refers to a chemical agent that donates electrons during an oxidation-reduction reaction. Reducing agents may include, but are not limited to sodium borohydride (NaBH$_4$) and sodium cyanoborohydride (NaCNBH$_3$). Pretreatment of subject samples with one or more reducing agents prior to GCD59 analysis may be carried out to alter the structure of glycated side chains. In some cases, detection antibodies of the present invention may be directed to GCD59 wherein K41 comprises glucitollysine. Assays comprising such detection antibodies may require that subject samples are reduced prior to analysis in order to reduce glycated K41. Some samples may be pretreated with NaCNBH$_3$. NaCNBH$_3$ pretreatment reduces glycated K41 residues comprising Schiff's bases to glucitollysine. Some samples may be pretreated with NaBH$_4$. NaBH$_4$ pretreatment reduces glycated K41 residues comprising Schiff's bases or Amadori Kits of the present invention may provide one or more reducing agents alone or in solution. Reducing agent solutions may comprise one or more of a variety of solvents. In some cases, reducing agent solutions comprise water as a solvent. In some cases, reducing agent solutions may comprise one or more organic solvents. Organic solvents are solvents comprising carbon-based components. Organic solvents may include, but are not limited to 1,1-dichloroethane, 1,2-dichloroethane, 1,2-dimethoxy-ethane, 1-butanol, 1-heptanol, 1-hexanol, 1-octanol, 1-pentanol, 1-propanol, 2-aminoethanol, 2-butanol, 2-butanone, bis(2-methoxyethyl) ether, 2-pentanol, 2-pentanone, 2-propanol, 3-pentanol, 3-pentanone, acetic acid, acetone, acetonitrile, acetyl acetone, aniline, anisole, benzene, benzonitrile, benzyl alcohol, carbon disulfide, carbon tetrachloride, chlorobenzene, chloroform, cyclohexane, cyclohexanol, cyclohexanone, diethyl ether, diethylamine, diethylene glycol, diglyme, dimethoxyethane (glyme), dimethyl sulfoxide (DMSO), dimethylether, N,N-dimethyl-formamide (DMF), N,N-dimethyl-acetamide, dimethylphthalate, dimethylsulfoxide (DMSO), di-n-butylphthalate, dioxane, ethanol, ether, ethyl acetate, ethyl acetoacetate, ethyl benzoate, ethylene glycol, glycerin, heptane, 2-ethylhexanol, Hexamethylphosphoramide, Hexamethylphosphorous triamide (HMPT), hexane, i-butanol, methanol, methyl acetate, methyl t-butyl ether (MTBE), methylene chloride, N,N-dimethylaniline, nitromethane, N-methyl-2-pyrrolidinone, pentane, Petroleum ether (ligroine), pyridine, t-butyl alcohol, tetraglyme, tetrahydrofuran (THF), toluene, triethyl amine, nitromethane and triethylene glycol dimethyl ether. In some embodiments, reducing agent solutions may comprise triethylene glycol dimethyl ether, and/or tetraglyme solvents.

Reducing agent solutions comprising organic solvents may include $NaBH_4$ solutions. The solubility of $NaBH_4$ in various organic solvents can be found on page 8 of Rohm and Haas: The Sodium Borohydride Digest, 2003. Commercial preparations of $NaBH_4$ may be used to prepare reducing agent solutions for sample treatment or to prepare reducing agent solutions to be included in kits of the present invention. Such commercial preparations may include, but are not limited to 99% Sodium Borohydride Solution 0.5 M in bis(2-methoxyethyl) ether; 99% Sodium Borohydride Solution 3 M in tetraglymeether; 99% Sodium Borohydride Solution 2.0 M in triethylene glycol dimethyl ether; 99.5% Sodium Borohydride Solution 0.5 M in bis(2-methoxyethyl) ether; 99.5% Sodium Borohydride Solution 3 M in tetraglymeether; 99.5% Sodium Borohydride Solution 2.0 M in triethylene glycol dimethyl ether; 99.9% Sodium Borohydride Solution 3 M in tetraglymeether; 99.9% Sodium Borohydride Solution 2.0 M in triethylene glycol dimethyl ether; 99.95% Sodium Borohydride Solution 0.5 M in bis(2-methoxyethyl) ether; 99.95% Sodium Borohydride Solution 3 M in tetraglymeether; 99.95% Sodium Borohydride Solution 2.0 M in triethylene glycol dimethyl ether; 99.99% Sodium Borohydride Solution 0.5 M in bis(2-methoxyethyl) ether; 99.99% Sodium Borohydride Solution 3 M in tetraglymeether; 99.99% Sodium Borohydride Solution 2.0 M in triethylene glycol dimethyl ether; 99.999% Sodium Borohydride Solution 0.5 M in bis(2-methoxyethyl) ether; 99.999% Sodium Borohydride Solution 3 M in tetraglymeether; 99.999% Sodium Borohydride Solution 2.0 M in triethylene glycol dimethyl ether; and 99.9% Sodium Borohydride Solution 0.5 M in bis(2-methoxyethyl) ether.

Reducing agent solutions prepared for sample treatment or prepared for inclusion in kits of the present invention may comprise from about 0.1 M to about 10 M concentrations of reducing agent. In some cases, reducing agent solutions of the present invention may comprise stock solutions that require dilution before being used to treat samples. Reducing agent stock solutions of the present invention may comprise greater than 1 M concentrations of reducing agents, including, but not limited to 1.5 M, 2 M, 3 M, 4 M, 5 M or 10 M. In some cases, reducing agent stock solutions are diluted to 0.5 M to 1 M reducing agent concentrations prior to sample treatment. Dilution may be carried out using the same solvent found in stock solutions or with a different solvent. For example, stock solutions comprising organic solvents may be diluted with water prior to sample treatment.

In some cases, subject samples may be combined with 1 M concentrations of reducing agent at a ratio of from about 1:1 to a ratio of about 1:1000 sample to reducing agent. Some subject samples may be combined at a ratio of about 1:5, 1:10, 1:20, 1:100 or 1:500 with 1 M concentrations of reducing agent. After combining, subject sample-reducing agent solutions may be incubated from about 20 minutes to about 2 hours, from about 1 hour to about 4 hours, from about 3 hours to about 24 hours, from about 12 hours to about 3 days, from about 2 days to about 5 days or at least 5 days to allow sample reduction to occur.

Applications

GCD59 detection kits of the present invention may be used to detect and/or quantitate GCD59 in one or more samples. Such samples may be derived from one or more subjects. Some subjects may include female subjects, pregnant subjects, postpartum subjects and/or infant subjects.

GCD59 concentration levels determined by one or more kits of the present invention may be useful for diagnosis of one or more disease, disorder and/or condition. As such, some embodiments of the present invention may comprise methods of diagnosing one or more disease, disorder and/or condition using one or more kits of the present invention. In some cases, GCD59 concentration levels determined by one or more kits of the present invention may be useful for determining the risk of developing one or more disease, disorder and/or condition. Also herein are methods of determining the risk of developing one or more disease, disorder and/or condition using one or more kits of the present invention. GCD59 concentration levels determined by one or more kits of the present invention may be useful for determining the severity of one or more disease, disorder and/or condition afflicting one or more subjects. As such, methods of the present invention may comprise determining the severity of one or more disease, disorder and/or condition afflicting one or more subject using one or more kits of the present invention. In some cases, GCD59 concentration levels determined by one or more kits of the present invention may be useful for monitoring the onset, progression or regression of one or more disease, disorder and/or condition afflicting one or more subjects. As such, embodiments of the present invention may comprise methods for monitoring the onset, progression or regression of one or more disease, disorder and/or condition afflicting one or more subject using one or more kits of the present invention.

In some embodiments, GCD59 concentration levels determined by one or more kits of the present invention may be useful for determining the course of treatment for one or more disease, disorder and/or condition afflicting one or more subjects. As such, the present invention may comprise methods of determining the course of treatment for one or more disease, disorder and/or condition afflicting one or more subject using one or more kits of the present invention and treating such subjects accordingly. Also provided are methods of reducing, reversing and/or preventing one or more disease, disorder and/or condition comprising the steps of determining the presence and/or concentration of GCD59 in one or more subject samples, determining the risk, presence and/or progression of one or more disease, disorder and/or condition in said subjects and treating subjects accordingly.

Some methods of the present invention may comprise internal controls of GCD59 prepared from plasma samples from individuals with diabetes. As used herein, the term "internal control" refers to one or more samples used in an assay as a point of reference and/or comparison in order to make judgements as to the presence, absence or level of one or more factors being analyzed. Some internal control samples may comprise negative or positive control samples. Negative control samples are samples known to lack one or more factors being analyzed. Positive control samples are samples known to comprise one or more factors being analyzed. Such controls may comprise different concentrations of GCD59 (e.g., low, medium and high). In some embodiments, GCD59 internal controls may be obtained from pooled plasma samples from individuals with diabetes. Analysis values obtained with GCD59 internal controls may be used to accept or reject individual analyses, according to pre-specified criteria. Such criteria may include, but are not limited to Westgard rules as disclosed by Westgard et al. (Westgard, J. O. et al., 1981. Clin Chem; 27:493-501, the contents of which are herein incorporated by reference in their entirety).

In some cases, methods of the present invention may be carried out according to any of those described by Ghosh et al. (Ghosh et al., 2013. Am. J. Hematol. 88:670-6, the contents of which are herein incorporated by reference in their entirety).

Diabetes

In some embodiments, kits of the present invention may be useful in the detection, diagnosis and/or prognosis of diabetes. Diabetes is a disease characterized by elevated blood glucose levels, also referred to as hyperglycemia. Insulin, along with other hormones including, but not limited to glucagon and epinephrine, is critical for maintenance of normal glucose levels in the blood. Insulin binding to cellular receptors facilitates cellular uptake of glucose, providing an energy source for cells and lowering glucose levels in the blood (Rodger, W., CMAJ. 1991. 145(10):1227-37). Insulin is expressed by pancreatic R cells and its expression is upregulated when blood glucose levels rise. In diabetes, insulin levels and/or sensitivity to insulin are disrupted, reducing cellular glucose uptake and elevating circulating levels of glucose. The two primary forms of diabetes are insulin-dependent (also referred to herein as juvenile diabetes or Type I diabetes) and insulin-independent (also referred to herein as adult-onset diabetes or Type II diabetes). Type I diabetes is less common and typically brought on by autoimmune destruction of β cells, the primary source of insulin. 90% or more of those with diabetes suffer from Type II diabetes. This form of the disease is characterized by reduced insulin secretion and/or reduced sensitivity to insulin (e.g., reduced ability of insulin to stimulate glucose uptake in cells) (Rodger, W., Non-insulin-dependent (Type II) diabetes mellitus. CMAJ. 1991. 145(12)1571-81). Type II diabetes is thought to occur in part due to genetic susceptibility and occurs most often in subjects who are overweight and/or obese.

The term "diabetic" as used herein, refers to an individual comprising one or more types of insulin deficiency (e.g., reduced insulin levels and/or reduced insulin sensitivity). The term diabetic includes, but is not limited to, individuals with juvenile diabetes (Type I diabetes), adult-onset diabetes (Type II diabetes), gestational diabetes mellitus (GDM), and any other conditions of insulin deficiency. The term "diabetic" is a term of art, known and understood by those practicing in the medical profession, a formal definition of which can be found in Harrison's Principles of Medicine (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

Gestational Diabetes Mellitus (GDM)

In some embodiments, kits of the present invention may be useful in the detection, diagnosis and/or prognosis of gestational diabetes mellitus (GDM). As used herein, the terms "gestational diabetes mellitus" or "GDM" refer to a diabetic condition characterized by elevated blood glucose levels, carbohydrate intolerance and/or reduced insulin sensitivity that is brought on by pregnancy. In some cases, GDM diagnosis in each country may rely on different standards set by the professional bodies from such countries that issue recommendations to physicians practicing there. GDM may affect up to 18% of pregnancies with adverse outcomes that affect both the mother and offspring, including both short term and long term effects. Currently, diagnosis and monitoring of GDM in female subjects relies heavily on the measurement of blood glucose levels. Blood glucose is in constant flux and influenced by a number of external factors including meals and level of activity. Glucose levels may change on an hourly basis. This complicates GDM testing by imposing diet requirements and/or restrictions on subjects undergoing testing.

GDM is one of the most prevalent disorders affecting pregnant women and carries with it a greater risk for complications during pregnancy, at the time of birth and even after birth. Additionally, such complications may affect both mother and offspring. Individuals with GDM lack the ability to adequately break down carbohydrates into energy (Okun, N., Can Fam Physician. 1997. 43:88-93). In some cases, GDM diagnosis may be carried out through the detection of high blood glucose levels and/or through the observation of a decreased ability to respond to a glucose challenge during pregnancy. Such diagnosis occurs most often in the third trimester. Although mechanisms leading to GDM are still unclear, in some cases, it is believed that hormones that become elevated during pregnancy may interfere with normal insulin signaling, including, but not limited to insulin resistance. This insulin signaling dysfunction leads to decreased cellular glucose uptake and elevated blood glucose levels. Studies disclosed herein indicate that GCD59 levels are elevated in subjects comprising GDM.

GDM Screening and Diagnosis

GDM is one of the most common medical complications of pregnancy. In each country, GDM diagnosis may be determined by standards set by professional bodies responsible for issuing recommendations to practicing physicians in each country. There is ongoing debate among professional bodies within the United States as well as between professional bodies in the United States and those abroad as to how to approach GDM diagnosis. Such US professional bodies may include, but are not limited to the National Institutes of Health (NIH), the American Diabetes Association (ADA) and the American Congress of Obstetricians and Gynecologists (ACOG). Such International bodies may include, but are not limited to the International Association of Diabetes and Pregnancy Study Groups (IADPSG). Professional bodies in the US and abroad may tailor their approaches based on different studies, different analysis of such studies and may be affected by health care and economic pressures. Indeed, factors for defining GDM and criteria for diagnosis may change over time. As such, in some embodiments, diagnostic tests for GDM described herein may be conducted in accordance with the most current recommendations issued by professional bodies in each country involved in the health of pregnant women, fetuses, and newborns.

According to some current US practices, screening of all pregnant women for GDM is suggested. In some cases, screening may comprise a review of patient history, assessment of clinical risk factors and/or one or more tests comprising a glucose challenge. As used herein, the term "glucose challenge" refers to a testing component characterized by the administration of glucose to a subject. Glucose challenge testing typically assesses the response in subjects to a glucose challenge. This may comprise analyzing blood glucose levels. The amount of glucose administered during a glucose challenge may vary. Typical tests comprise the administration of from about 50 g to about 100 g of glucose. In other embodiments, 75 g of glucose are administered. In some cases, GCD59 levels may be assessed after one or more glucose challenge or after a meal.

"Low risk" pregnant subjects, at the lowest risk of developing GDM, comprise those who are less than 25 years old, have normal body weight, have no family history of diabetes (at the level of frist-degree relatives,) do not have a history of abnormal glucose metabolism, do not have a history of poor obstetric outcome and are not of a high risk ethnicity (e.g. Hispanic, Native American, African American and South Asian). Pregnant subject risk assessment is typically carried out during a first prenatal visit. Women at higher risk of developing GDM (e.g., obese, personal history of GDM, glycosuria, family history of diabetes, etc.) typically undergo testing as soon as possible. If initial tests in such women are negative, retesting is recommended between the $24^{th}$ and $28^{th}$ weeks of pregnancy.

Plasma glucose levels may be indicative of GDM in the absence of a glucose challenge. Some methods disclosed herein comprise fasting glucose tests. According to such tests, fasting plasma glucose (FPG) levels may be determined. Fasting plasma glucose levels refer to levels of glucose measured directly after a period of fasting. Periods of fasting may be from about 1 hour to about 24 hours. In certain embodiments, FPG levels may be measured after about 12 hours of fasting. In pregnant subjects, fasting plasma glucose levels that are greater than 126 mg/dl indicate gestational diabetes.

In some embodiments, random glucose tests may be conducted. Such tests measure random plasma glucose levels (also referred to as casual plasma glucose levels). Random glucose levels refer to glucose levels obtained without any consumption restrictions and/or requirements (e.g., fasting). In pregnant subjects, random plasma glucose levels that are greater than 200 mg/dl indicate GDM in such subjects. In certain embodiments, a second measurement is required the next day for both FGP levels and random plasma levels to confirm diagnosis of GDM. In some embodiments of the present invention, GCD59 levels may also be obtained without consumption restrictions and/or requirements (e.g., fasting).

In cases where hyperglycemia is more subtle, other approaches may be necessary for diagnosis. In pregnant subjects identified as being high risk, the one-step approach may be sufficient. According to the one-step approach, diagnosis may be carried out by oral glucose tolerance testing (OGTT) without any prior blood glucose screening. For individuals of average risk, the two-step approach is typically carried out. According to the two-step approach, an initial screening comprising a glucose challenge is carried out. In initial screenings of the two-step approach, Recommendations by the American College of Obstetricians made in 2001 call for a 50 g, one hour oral glucose challenge test (GCT) to be used (Committee on Obstetric Practice, The American College of Obstetricians and Gynecologists: Committee Opinion. 2011). The one hour oral GCT measures blood glucose concentrations 1 hour after the oral administration of 50 g of glucose. 80% of pregnant subjects with GDM comprise blood glucose levels above the cut-off value of 130 mg/dl and 90% comprise levels above the cut-off value of 140 mg/dl. As used herein, the term "cut-off value" refers to a value or level at which an indication may be made with regard to a diagnostic determination or other type of determination, wherein a level below a given cut-off leads to a determination that is different from a determination based of a level above a given cut-off (American Diabetes Association, Diabetes Care. 31(1):S62-S67).

In the second step of the two-step approach, a 100 g OGTT is carried out. As used herein, the term "oral glucose tolerance test" or "OGTT" refers to a test that measures the ability of the body to utilize glucose. Such testing typically begins in the morning, wherein the subjects have not eaten for 8-12 hours. A baseline concentration is established based on an initial blood sample. As used herein, the term "baseline" when referring to measurements, levels or values refers to an initial measurement, level or value to which subsequent measurements, levels or values may be compared. After the initial blood sample is taken, subjects are given a glucose solution to drink with a measured concentration of glucose. In the 100 g OGTT, 100 g of glucose is administered in the glucose solution. Subjects are typically required to finish the drink within a 5 minute time frame. Finally, OGTTs comprise the obtaining of subsequent blood samples to monitor blood glucose and/or insulin levels. According to the 100 g OGTT, diagnosis of GDM in pregnant subjects may be made when subject blood glucose levels exceed a cut-off value of 95 mg/dl for baseline readings, a cut-off value of 180 mg/dl one hour after glucose administration, a cut-off value of 155 mg/dl two hours after glucose administration and/or a cut-off of 140 mg/dl three hours after glucose administration. In some embodiments, a diagnosis of GDM may require that two out of four tests yield elevated blood glucose levels.

In some cases, a 75 g OGTT is carried out in the second step of the two step approach to GDM diagnosis. The 75 g OGTT is carried out according to the 100 g OGTT with the exception that only 75 g of glucose are administered. According to the 75 g OGTT, diagnosis of GDM in pregnant subjects may be made when subject blood glucose levels exceed a cut-off value of 95 mg/dl for baseline readings, a cut-off value of 180 mg/dl one hour after glucose administration and/or a cut-off value of 155 mg/dl two hours after glucose administration. In some embodiments, a diagnosis of GDM may require that two out of four tests yield elevated blood glucose levels.

In some cases, the 2-hour postprandial glucose test is carried out during GDM screening. 2-hour postprandial glucose testing comprises the analysis of blood glucose levels 2 hours after a meal.

In some cases, 1,5-anhydroglucitol testing may be carried out during GDM screening. Levels of 1,5-anhydroglucitol levels are reduced during periods of hyperglycemia (wherein blood glucose levels are above 180 mg/dl), requiring up to 2 weeks to return to normal after hyperglycemic conditions have ended (McGill, J. B. et al., Diabetes Care. 2004. 27(8):1859-65). 1,5-anhydroglucitol testing may be done to determine whether subject have endured extended periods of hyperglycemia.

In some cases, hemoglobin A1c (HbA1c) testing may be carried out during GDM screening. Such testing measures the level of a glycated version of hemoglobin, HbA1c in the blood. HbA1c levels increase during periods of hyperglycemia. HbA1c remains in the blood from about 8 to about 12 weeks until red blood cells comprising HbA1c are replaced, making HbA1c a good longer term reading of overall blood glucose levels during that period (http://medweb.bham.ac.uk/easdec/prevention/what_is_the_hba1c.htm).

In some embodiments, fructosamine testing may be carried out during GDM screening. Fructosamine levels become elevated under hyperglycemic conditions. Elevated levels of fructosamine remain elevated for two to three weeks after hyperglycemic conditions subside, making them a good longer term indicator of high blood glucose levels (Delpierre, G. et al., Biochem J. 2002. 365:801-8).

In some embodiments, subject samples may be obtained and analyzed prior to pregnancy. Such subject samples may be obtained from a female subject. Subject samples may also be used to determine a level of risk of developing GDM and/or pre-eclampsia in a later pregnancy.

In some embodiments, kits and methods of the present invention for determining GCD59 levels may be combined with any of the tests described herein. Such tests may include, but are not limited to glucose challenge testing, oral glucose tolerance testing, fasting glucose testing, random glucose testing, 2-hour postprandial glucose testing, hemoglobin A1c (HbA1c) testing, fructosamine testing and 1,5-anhydroglucitol testing. In some embodiments, kits and methods of the present invention for determining GCD59 levels may be combined with such tests for the purposes of diagnosis, prognosis and/or monitoring of GDM or other diabetic conditions.

Kits and methods of the present invention for determining GCD59 levels may be combined with detection of other glycated proteins. Many other proteins present within bodily fluids comprise amino groups that may be capable of being glycated. Such proteins may include glycated albumin, glycated hemoglobin, glycated immunoglobulins, glycated hemopexin, glycated vitamin D binding protein, glycated fibrinogen alpha chain, glycated apolipoprotein A1, glycated transferrin, glycated macroglobulin alpha 2, glycated complement component 4A, glycated fibrinogen beta chain, glycated fibrinogen alpha chain, glycated abhydrolase domain-containing protein 1 4B, glycated amiloride-sensitive amine oxidase copper-containing precursor, glycated angiotensin-converting enzyme isoform 1 precursor, glycated peptidase family M2 Angiotensin converting enzyme, glycated aconitase 1, glycated lysosomal acid phosphatase isoform 1 precursor, glycated pancreatitis-associated protein, glycated alpha-actinin-4, glycated metalloproteinase with thrombospondin type 1 motifs, glycated aspartylglucosaminidase, glycated adenosylhomocysteinase, glycated alpha-2-HS-glycoprotein, glycated alcohol dehydrogenase NADP$^+$, glycated aldo-keto reductase family 1, glycated aldehyde dehydrogenase family 1 member L1, glycated aldolase B fructose-bisphosphate, glycated pancreatic amylase alpha 2A, and glycated apolipoprotein A4 (Ukita et al., Clin. Chem. (1991) 37:504; Johansen et al., Glycobiol. (2006) 16:844; and Davies et al., J. Exp. Med. (1989) 170:637). In some embodiments, GCD59 may be detected as part of a panel or array of biomarkers comprising any of the glycated proteins listed above.

GDM Categories

In some embodiments, pregnant subjects may be placed into different subcategories of disease based on certain criteria. Two such categories include those with impaired glucose tolerance (IGT) and those with impaired fasting glucose (IFG). These categories are designated for subjects whose glucose levels are above normal, but do not rise to the level of GDM or that fall short of the requirement for GDM diagnosis. Factors determining placement of subjects into such categories may be different for each country and may be controlled by professional bodies in such countries responsible for providing recommendations to physicians practicing in such countries.

In some embodiments, pregnant subjects may be diagnosed with IFG when fasted glucose levels in such subjects comprise from about 100 mg/dl to about 125 mg/dl as compared to those with normal fasted glucose levels (less than 100 mg/dl) and those whose levels lead to a provisional diagnosis of GDM (in some cases with levels greater than 126 mg/dl). In some cases, pregnant subjects may be diagnosed with IGT after OGTT results. In some cases, pregnant subjects with IGT may comprise blood glucose levels from about 140 mg/dl to about 199 mg/dl two hours after glucose administration as compared to those with normal levels (in some cases with levels less than 140 mg/dl) and those whose levels lead to a provisional diagnosis of GDM (in some cases with levels greater than 200 mg/dl).

In some embodiments, pregnant subjects with IGT and/or IFG are referred to as having pre-diabetes. As used herein, the term "pre-diabetes" refers to a condition characterized by high risk for developing diabetes (American Diabetes Association, Diabetes Care. 2008. 31(1):S62-S67). Factors determining designation of subjects into the category of pre-diabetes may be different for each country and may be controlled by professional bodies in such countries responsible for providing recommendations to physicians practicing in such countries.

In some cases, pregnant subjects suffering from GDM may be assigned to a category comprising a class of GDM developed by Dr. Priscilla White, refered to herein as "White's GDM class" (Dunn, P. M., Dr. Priscilla White (1900-1989) of Boston and pregnancy diabetes. Arch Dis Child Fetal Neonatal Ed. 2004 May; 89(3):F276-8, herein incorporated by reference in its entirety). Such GDM classes may include any of those listed in Table 1.

TABLE 1

| GDM classes | |
|---|---|
| Class | Description |
| A1 | insulin independent |
| A2 | insulin dependent |
| B | diabetic <10 years, onset after age 20 |
| C | diabetic 10-19 years, onset between ages 10-19, no vascular complications |
| D | diabetic >20 years, onset before age 10, with vascular complications |
| F | with nephropathy |
| R | with retinopathy |
| T | with prior kidney transplant |
| H | with heart disease |

White's GDM classes include Class A1, Class A2, Class B, Class C, Class D, Class F, Class R, Class T and Class H. Of these, Class A1 and Class A2 are used to classify subjects with GDM, but not pre-existing diabetes. The other Classes are used to categories pregnant subjects that suffer from diabetes that developed at some point prior to pregnancy.

In some embodiments, GDM may be categorized according to two or more levels of GDM severity. As used herein, the term "level of GDM severity" refers to a category of disease characterized by different levels of complications or negative outcomes, typically from less severe to more severe. GDM severity may be assigned based on the level of one or more factors that correlate with such complications or negative outcomes. In other embodiments, GDM severity may be assigned based on the metabolism of blood glucose. GDM severity may also be determined by levels of GCD59. In such embodiments, mild, moderate and severe GDM levels may be assigned to subjects depending on where concentration levels of GCD59, obtained from subject samples, fall between predetermined cut-off values.

Preliminary Indications and Risk Factors

Typically there are no symptoms for GDM. In some cases symptoms do occur and include, but are not limited to thirst, fatigue, nausea, vomiting, bladder infection, yeast infection and blurred vision (http://www.nlm.nih.gov/medlineplus/ency/article/000896.htm). Preliminary indications of disease typically involve test results (e.g., elevated glucose levels, elevated levels of glycated proteins).

Risk factors for GDM may include, but are not limited to elevated body mass index (BMI), family history of diabetes or GDM, advanced maternal age, a history of polycystic ovary syndrome, a history of smoking, a history of obstetric issues, high cholesterol, short stature and ethnicity (Ross, G., Australian Family Physician. 2006. 35(6):392-6; Bjorge, T. et al., Am J Epid. 2004. 160(12):1168-76; Ma, R. M. at al., Diabetes Care. 2007. 30(11):2960-1). In some cases, the presence or absence of risk factors may influence one or more course of action with regard to testing and/or treatment of female subjects.

As used herein, the term "body mass index" refers to a number calculated from a subject's weight and height that correlates with the level of body fat of a given subject. This value is obtained from a subject by dividing the weight of the subject in kilograms by (height)$^2$ in meters. In some cases, BMI values may be interpreted as follows: below 18.5 kg/m$^2$—underweight; 18.5 kg/m$^2$-24.9 kg/m$^2$—normal; 25.0 kg/m$^2$-29.9 kg/m$^2$—overweight; 30.0 kg/m$^2$-34.9 kg/m$^2$—grade I obesity; 35.0 kg/m$^2$-39.9 kg/m$^2$—grade II obesity and above 40 kg/m$^2$—grade III obesity. According to such interpretations, subjects who are overweight comprise a 2.14-fold increased risk of developing GDM (Yessoufou, A. et al., Experimental Diabetes Research. 2011. 2011:1-12). Subjects who are obese comprise a 3.56-fold increased risk of developing GDM and subjects who are severely obese comprise an 8.56-fold increased risk of developing GDM. BMI interpretations may be different in each country and may be determined by professional bodies responsible for setting guidelines for physicians practicing within such countries and/or governing bodies.

Pregnant subjects with a history of pre-diabetes and/or GDM have a higher risk of developing GDM. Additionally, pregnant subjects with a family history of diabetes, pre-diabetes and/or GDM have a higher risk of developing GDM. Subject history and/or family history are typically reviewed during the first prenatal appointment. In some embodiments, subject history and/or family history may be used to make decisions about subject testing and/or treatment.

Advanced maternal age is also a risk factor for developing GDM. The percent of pregnant subjects with GDM varies among different age groups (Ross, G., Australian Family Physician. 2006. 35(6):392-6). About 1% of pregnant subjects under 20 develop GDM during pregnancy, while about 1.8% of pregnant subjects from ages 20 to 24 develop GDM, about 2.5% of pregnant subjects from ages 25 to 29 develop GDM, about 4.1% of pregnant subjects from ages 30 to 34 develop GDM, about 6.5% of pregnant subjects from ages 35 to 39 develop GDM, about 9.8% of pregnant subjects from ages 40 to 45 develop GDM and about 12.8% of pregnant subjects over 45 develop GDM.

Rates of GDM are also influenced by ethnicity with higher incidence in pregnant subjects who are African American, Native American, Hispanic and South Asian (including, but not limited to Pacific Islanders)(Kim, S. Y. et al., Prev Chronic Dis. 2012. 9:E88).

GDM-Related Conditions

GDM is a major cause of peri- and post-natal complications for mothers and their offspring. Pregnant subjects afflicted with GDM may face complications at delivery, increased number of C-sections, risk of pre-eclampsia/eclampsia, miscarriage and/or post-pregnancy diabetes. Infant subjects born to pregnant subjects afflicted with GDM may face macrosomia, birth defects, birth trauma, hyperbilirubinemia, hypoglycemia, seizures and still birth.

One of the main adverse outcomes associated with GDM is macrosomia. As used herein, the term macrosomia refers to a condition in infant subjects characterized by large birth weight. Large birth weight, as used herein refers to birth weights above about 8 pounds, 13 ounces or roughly above 4 kg. As used herein, the term "infant subject" refers to subjects who are infants and embraces subjects from birth to about 1 year of age. Infant subjects characterized with macrosomia comprise about 10% of total births. Often, abnormal or difficult childbirth (also referred to herein as dystocia) and/or birth trauma associated with infant subjects born to pregnant subjects with GDM are due to the large size of such infant subjects, causing physical stress during birth to both the mother and offspring (Najafian, M. et al., Obstetrics and Gynecology. 2012. 2012:353791). In pregnant subjects suffering from GDM, elevated blood glucose levels typically lead to increased glucose and nutrient transport across the placenta to the developing offspring (Yessoufou, A. et al., Experimental Diabetes Research. 2011. 2011:1-12). Excess nutrient levels in the developing offspring may also put such offspring in danger of developing hypoglycemia, or low blood glucose, after birth. Increased nutrient levels in utero lead to elevated insulin production by developing offspring. After birth, the transfer of placental nutrients ceases, and elevated circulating insulin in infant subjects causes blood glucose levels to drop.

Pregnancy-related hypertensive disorders, such as pre-eclampsia have also been shown to be related to GDM (Feig, D. S. et al., PLoS Med. 2013. 10(4): e1001425.) Pre-eclampsia is a serious medical condition in pregnant subjects characterized by elevated blood pressure and proteinuria (protein in the urine). Studies indicate that pregnant subjects with GDM have a higher risk of developing pre-eclampsia. It has also been shown that the risk of pre-eclampsia increases with intolerance to glucose. Additionally, pregnant subjects with pre-eclampsia have been shown to have a higher incidence of insulin resistance.

Gestational Windows

In the context of embodiments of the present invention, the length of time comprising pregnancy may be divided into two or more gestational windows. As used herein, the term "gestational window" refers to any temporally, developmentally and/or physiologically defined period of a pregnancy. Gestational windows may comprise weeks of pregnancy. The typical term of a human pregnancy is from about 40 to about 42 weeks (but may extend beyond 42 weeks in some cases) and is calculated starting with the end of the last menstrual cycle of a pregnant subject. As such, gestational windows may comprise from about 0 to about 46, from about 0 to about 42, from about 2 to about 42, from about 4 to about 42, from about 8 to about 42, from about 12 to about 42, from about 16 to about 42, from about 20 to about 42, from about 24 to about 42, from about 28 to about 42, from about 32 to about 42, from about 36 to about 42, from about 12 to about 36, from about 16 to about 36, from about 20 to about 36, from about 24 to about 36, from about 10 to about 28, from about 16 to about 28, from about 20 to about 28, from about 16 to about 24, or from about 18 to about 24 weeks of pregnancy. In some cases, gestational windows may comprise week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, week 25, week 26, week 27, week 28, week 29, week 30, week 31, week 32, week 33, week 34, week 35, week 36, week 37, week 38, week 39, week 40, week 41, week 42, week 43, week 44, week 45, week 46 or after week 46 of pregnancy. Gestational windows may also comprise months of pregnancy. The typical term of a pregnancy is 9-10 months. As such, gestational windows may comprise from about month 1 to about month 10, from about month 2 to about month 10, from about month 3 to about month 10, from about month 4 to about month 10, from about month 5 to about month 10, from about month 6 to about month 10, from about month 7 to about month 10, from about month 8 to about month 10, from about month 9 to about month 10, from about month 1 to about month 9, from about month 2 to about month 9, from about month 3 to about month 9, from about month 4 to about month 9, from about month 5 to about month 9, from about month 6 to about month 9, from about month 7 to about month 9, from about month 8 to about mount 9, from about month 1 to about month 6, from about month 1 to about month 4, from about month 1 to about month 3, from about month 3 to about month 9, from about month 3 to about month 6, from about month 4 to about month 6, from about month 3 to about month 7, from about month 2 to about month 7 or from about month 2 to about month 6 of pregnancy. In some cases, gestational windows may comprise month 1, 2, 3, 4, 5, 6, 7, 8, 9 or 10. In other embodiments, gestational windows may comprise trimesters. The term of a pregnancy may be divided into three trimesters. The first trimester may comprise from about 1 month to about 3 months of pregnancy and/or from about week 1 to about week 12 of pregnancy. During the first trimester, typical development comprises fetal growth to a weight of about 28 g (or about 1 ounce) and a length from about 7.6 cm to about 10 cm (or from about 3 to about 4 inches) long. The second trimester may comprise from about 4 months to about 6 months of pregnancy and/or from about 13 weeks to about 28 weeks of pregnancy. During the second trimester, typical development comprises fetal growth to a weight of about 910 g (or about 2 pounds) and length from about 23 cm to about 31 cm (or from about 9 inches to about 12 inches) long. The third trimester may comprise from about 7 months to about 9 months of pregnancy and/or from about 29 to about 40 weeks of pregnancy. During the third trimester, typical development comprises fetal growth to a weight of about 3.2 kg (or about 7 pounds) and length from about 45 cm to about 51 cm (or from about 18 to about 20 inches) long.

In some embodiments, gestational windows may comprise stages of fetal development. Such stages may include, but are not limited to blastocyst formation, placental formation, embryo formation, heart development, lung development, liver development, kidney development, gastrointestinal development and nervous system development.

Monitoring and Therapy

Analyses disclosed herein may comprise the use of a single sample obtained from a subject. Such samples may comprise bodily fluid samples. Bodily fluid samples may include, but are not limited to blood, urine, mucous, amniotic fluid, saliva and/or other sample types disclosed herein. Biomarker levels may be analyzed in a single subject sample or in multiple subject samples. GCD59 levels, for example, may be monitored over time. As used herein, the term "monitoring" refers to the act of observing, evaluating and/or measuring over time. Observing, evaluating and/or measuring may be recorded in the form of one or more amounts or values.

In some embodiments, values for the purposes of monitoring may comprise concentration values. Monitoring is typically carried out by obtaining initial or baseline values by which subsequent values may be compared. During monitoring, one or more subsequent values may be obtained and compared to baseline values and/or any other previously obtained values. Subsequent values may be obtained for the purposes of short-term comparisons, long-term comparisons, weekly comparisons, monthly comparisons and the like. Short-term comparisons may be used to monitor one or more biomarker levels in subject samples in response to a particular challenge (e.g., a glucose challenge) to the subject. Such subject samples may be obtained every 10, 20, 30, 40, 50, 75 and/or 150 minutes and analyzed to generate subsequent values for comparison. Subject samples for short-term comparisons may be obtained every 1, 2, 3, 4, 5, 10, 12 and/or 24 hours for the generation of subsequent values. Such subject samples may comprise blood, urine, mucous, amniotic fluid, saliva and/or any other bodily fluids disclosed herein. Glucose levels and/or levels of glycated proteins may also be obtained from such samples. In some cases, levels of GCD59 (including, but not limited to concentration values) may be obtained from subject samples for short-term comparisons.

In some embodiments, long-term comparisons may be used to monitor one or more biomarker levels/concentrations in subjects. Subsequent values obtained for long-term comparisons may be obtained each week, each month, each quarter, each year and/or at least each year. Long-term comparisons may comprise subsequent values obtained from subject samples obtained about 2 weeks to about 2 months apart. Such subject samples may comprise bodily fluids samples. Such bodily fluid samples may comprise blood, urine, mucous, amniotic fluid, saliva and/or any other bodily fluid samples disclosed herein. In some embodiments, glucose levels may be obtained from samples for long-term comparisons. In other embodiments, levels of glycated proteins may be obtained from samples for long-term comparisons. In further embodiments, GCD59 levels (e.g. GCD59 concentration levels) may be obtained.

In embodiments related to monitoring of GDM, observance, evaluation and/or measurement values may include, but are not limited to values reflecting weight, blood glucose levels, levels of glycated proteins (e.g., GCD59), biomarker levels, fetal weight, fetal size and BMI. Monitoring of GDM may be carried out through repeated tests and/or observations. Baseline values may be obtained prior to pregnancy, upon a first prenatal medical examination or within a given interval of pregnancy. Baseline values may, for example, be obtained from about 12 weeks to about 36 weeks of pregnancy, from about 20 weeks to about 36 weeks of pregnancy and/or from about 24 to about 28 weeks of pregnancy (including during week 24 of pregnancy, during week 25 of pregnancy, during week 26 of pregnancy, during week 27 of pregnancy and/or during week 28 of pregnancy). Some baseline values may be concentration values. Such concentration values may be obtained from a variety of sources. Baseline concentration values may also be obtained from bodily fluids including, but not limited to blood, urine, mucous, amniotic fluid, saliva and/or any other bodily fluid disclosed herein.

In some embodiments, baseline values may comprise the results of one or more tests used to evaluate one or more factors related to GDM. Such tests may include, but are not limited to glucose challenge testing (GCT,) the OGTT, the fasting glucose test, the random glucose test, the 2-hour postprandial glucose test, the HbA1c test, the fructosamine test and the 1,5-anhydroglucitol test.

During GDM monitoring, one or more subsequent values may be obtained and compared to baseline values and/or any other previously obtained values. Some subsequent values may be obtained for the purposes of short-term comparisons, long-term comparisons, weekly comparisons, monthly comparisons, trimester comparisons, transpartum comparisons (e.g., comparisons between pre- and post-delivery), transgestational comparisons (e.g., comparisons between pre-, peri- and/or post-pregnancy) and interpregnancy comparisons (e.g., between a first pregnancy and a second, third and/or fourth pregnancy). Short-term comparisons may be used to monitor one or more biomarker levels in response to a particular challenge (e.g., a glucose challenge) to the subject. Bodily fluid samples obtained for short-term comparisons may be obtained every 10, 20, 30, 40, 50, 75 and/or 150 minutes and analyzed to generate subsequent values for comparison. In other embodiments, bodily fluids for short-term comparisons may be obtained every 1, 2, 3, 4, 5, 10, 12 and/or 24 hours for the generation of subsequent values. Some bodily fluid samples for short-term comparisons may comprise blood, urine, mucous, amniotic fluid, saliva and/or any other bodily fluid disclosed herein. In some cases, glucose levels may be obtained from such samples. Levels of glycated proteins (including, but not limited to concentration values) may also be obtained from bodily fluids for short-term comparisons. Such levels may comprise GCD59 levels.

In some embodiments, long-term comparisons may be used to monitor one or more biomarker levels/concentrations in pregnant subjects. Subsequent values obtained for long-term comparisons may be obtained each week, each month, each trimester, each pregnancy and/or in each of pre-gestational, peri-gestational and post-gestational periods. Some long-term comparisons may comprise subsequent values obtained from subject samples obtained about 2 weeks to about 2 months apart. Some such subject samples may comprise bodily fluids samples. Such bodily fluid samples may comprise blood, urine, mucous, amniotic fluid, saliva and/or any other bodily fluids disclosed herein. In some cases, glucose levels may be obtained from samples for long-term comparisons. In other embodiments, levels of glycated proteins may be obtained from samples for long-term comparisons. In further embodiments, GCD59 levels (e.g., GCD59 concentration levels) may be obtained.

Monitoring may be carried out to observe the onset of one or more conditions and/or diseases. Some monitoring may be carried out to determine the onset of GDM and/or pre-eclampsia. In such embodiments, baseline values obtained may not indicate GDM and/or pre-eclampsia; however, subsequent values obtained may indicate onset. Onset may be determined by monitoring subject samples, including, but not limted to bodily fluids. Such bodily fluids may include blood, urine, mucous, amniotic fluid, saliva and/or any other bodily fluids disclosed herein. In some subject samples, glucose levels may be monitored to determine onset of GDM and/or pre-eclampsia. In other embodiments, levels of glycated proteins may be monitored to determine onset of GDM and/or pre-eclampsia. In further embodiments, GCD59 levels (e.g., GCD59 concentration levels) may be monitored to determine onset of GDM and/or pre-eclampsia.

In some embodiments, monitoring may be carried out to observe or assess the progression or regression of one or more conditions and/or diseases. Some monitoring may be carried out to observe or assess the progression or regression of GDM and/or pre-eclampsia. In such embodiments, baseline values obtained may indicate GDM and/or pre-eclampsia; however, subsequent values obtained may indicate progression or regression of disease. Progression or regression may be assessed by monitoring subject samples, including, but not limted to bodily fluids. Such bodily fluids may include blood, urine, mucous, amniotic fluid, saliva and/or any other bodily fluids disclosed herein. In some embodiments, glucose levels may be monitored to assess progression or regression of GDM and/or pre-eclampsia. In other embodiments, levels of glycated proteins may be monitored to assess progression or regression of GDM and/or pre-eclampsia. In further embodiments, GCD59 levels (e.g., GCD59 concentration levels) may be monitored to assess progression or regression of GDM and/or pre-eclampsia.

In some embodiments, monitoring may be carried out to observe or assess the progression of a diabetic condition in a postpartum subject. As used herein, the term "postpartum subject" refers to a subject that has recently given birth. Postpartum subjects may include subjects that have given birth in about the last hour, about the last day, about the last month, about the last 3 months and/or about the last year. Kits of the present invention may be used to determine GCD59 levels in one or more samples obtained from postpartum subjects. Such GCD59 levels obtained from one or more samples obtained from postpartum subjects may be used to diagnose, prognose or otherwise analyze one or more diabetic condition in such postpartum subjects.

In some embodiments, evaluation of subject samples may be carried out in order to apply an appropriate form of therapy. Such subject samples may be obtained from pregnant subjects with GDM. Therapeutic strategies for GDM may comprise diet modulation, increased activity, increased exercise, periodic blood glucose monitoring and/or insulin therapy. Selecting one or more therapeutic strategies based on evaluation of samples from a pregnant subject and applying one or more of the selected therapeutic strategies to the pregnant subject may prevent GDM-related conditions that effect infant subjects born to such pregnant subjects. Samples obtained from such pregnant subjects may be evaluated for levels of one or more biomarkers in order to select one or more therapeutic strategies. Such biomarkers may include glycated proteins, including, but not limited to GCD59. GCD59 concentration values obtained from pregnant subject samples may be used to select one or more therapies for the treatment of GDM. In such embodiments, one or more GDM-related conditions in infant subjects born to such pregnant subjects may be reduced, reversed and/or prevented.

Some methods of the present invention may be used to monitor subjects undergoing treatment for GDM. Such methods may comprise adjusting treatment dosages and/or types of therapy based on insights obtained from any of the types of monitoring described herein.

Companion Diagnostics

In some embodiments, assays of the present invention may be used as companion diagnositcs. As used herein, the term "companion diagnostic" refers to an assay, the results of which aid in the diagnosis or treatment of subjects. Companion diagnostics may be useful for stratifying patient disease, disorder or condition severity levels, allowing for modulation of treatment regimen and dose to reduce costs, shorten the duration of clinical trial, increase safety and/or increase effectiveness. Companion diagnostics may be used to predict the development of a disease, disorder or condition and aid in the prescription of preventative therapies. Some companion diagnostics may be used to select subjects for one or more clinical trials. In some cases, companion diagnostic assays may go hand-in-hand with a specific treatment to facilitate treatment optimization.

In some embodiments, GCD59 detection assays of the present invention may be useful as companion diagnostics for diseases, disorders and/or conditions related to glycemic levels. Some companion diagnostics of the present invention may be useful for predicting and/or determining the severity of diabetes, pre-diabetes or other diabetic conditions including, but not limited to GDM. Some companion diagnostics of the present invention may be used to stratify subjects by risk of developing diabetic complications. Such diabetic complications may include, but are not limited to diabetic ketoacidosis, hyperglycemia, hypoglycemia, hyperglycemia hyperosmolar state, diabetic coma, infections of the respiratory tract, gum disease, heart damage, kidney damage, decreased sensation, vision loss, cardiovascular disease, muscle deterioration and stroke. Some companion diagnostics of the present invention may be used to facilitate and expedite drug development for anti-diabetic and metabolic disease drugs.

Point of Care Testing

In some embodiments, kits and assays described herein may be used for point-of-care testing. As used herein, the term "point-of-care testing" refers to medical testing that is carried out at or near a site where a subject is receiving medical care. Point-of-care testing may facilitate shorter intervals between testing, review of test results and treatment. Point-of-care testing may also allow for patients to be tested and receive treatments determined by the results of such testing during the same day and/or during the same medical visit.

Definitions

Animal: As used herein, the term "animal" refers to any member of the animal kingdom. In some embodiments, "animal" refers to humans at any stage of development. "Animal" also may refer to non-human animals at any stage of development. In certain embodiments, non-human animals are mammals (e.g., rodents, mice, rats, rabbits, monkeys, dogs, cats, sheep, cattle, primates, or pigs). Some animals may include, but are not limited to, mammals, birds, reptiles, amphibians, fish, and worms. Some animals are transgenic animals, genetically-engineered animals, or clones.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity or hydrophobic interaction sufficiently stable such that the "associated" entities remain physically associated.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance, immunological detection and the like. Detectable labels may include radioisotopes, fluorophores, chromophores, enzymes, dyes, metal ions, ligands, biotin, avidin, streptavidin and haptens, quantum dots, polyhistidine tags, myc tags, flag tags, human influenza hemagglutinin (HA) tags and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Epitope: As used herein, an "epitope" refers to a surface or region on a molecule that is capable of interacting with one or more components of the immune system, including, but not limited to antibodies. In some embodiments, when referring to a protein or protein module, an epitope may comprise a linear stretch of amino acids or a surface patch formed by a three dimensional structure formed by a folded amino acid chain or chains.

Feature: As used herein, a "feature" refers to a characteristic, a property, or a distinctive element.

Fragment: A "fragment," as used herein, refers to a portion. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. Antibody fragments may include portions of an antibody subjected to enzymatic digestion or synthesized as such.

Gestational: As used herein, the term "gestational" means in relation to the term of a pregnancy, such that "pre-gestational" refers to one or more time periods before a pregnancy, "peri-gestational" refers to the time period comprising pregnancy and "post-gestational" refers to one or more time periods after pregnancy.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two amino acid sequences, for example, may be performed by aligning the two sequences for optimal comparison purposes (e.g., gaps can be introduced in one or both of a first and a second amino acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding amino acid residue positions are then compared. When a position in the first sequence is occupied by the same amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined, for example using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine identity between two sequences include, but are not limited to, GCG program package, Devereux, J., et al., *Nucleic Acids Research,* 12(1), 387 (1984), BLASTP, BLASTN, and FASTA Altschul, S. F. et al., *J. Molec. Biol.,* 215, 403 (1990).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, a, ab 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art. In some embodiments, isolation of a substance or entity includes disruption of chemical associations and/or bonds. In certain embodiments, isolation may include only the separation from components with which the isolated substance or entity was previously combined and does not include such disruption.

Modified: As used herein, the term "modified" refers to a changed state or structure of a molecule or entity as compared with a parent or reference molecule or entity. Molecules may be modified in many ways including chemically, structurally, and functionally. In some embodiments, compounds and/or compositions of the present invention are modified by the introduction of non-coded amino acids.

Mutation: As used herein, the term "mutation" refers to a change and/or alteration. Mutations may be changes and/or alterations to proteins (including peptides and polypeptides) and/or nucleic acids (including polynucleic acids). Some mutations comprise changes and/or alterations to protein and/or nucleic acid sequences. Such changes and/or alterations may comprise the addition, substitution and/or deletion of one or more amino acids (in the case of proteins and/or peptides) and/or nucleotides (in the case of nucleic acids and/or polynucleic acids). In embodiments wherein mutations comprise the addition and/or substitution of amino acids and/or nucleotides, such additions and/or substitutions may comprise 1 or more amino acid and/or nucleotide residues and may include modified amino acids and/or nucleotides.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep, water buffalo, and yak.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Peptide: As used herein, the term "peptide" refers to a chain of amino acids that is less than or equal to about 50 amino acids long, e.g., about 5, 10, 15, 20, 25, 30, 35, 40, 45, or 50 amino acids long.

Protein of interest: As used herein, the terms "proteins of interest" or "desired proteins" include those provided herein and fragments, mutants, variants, and alterations thereof.

Region: As used herein, the term "region" refers to a zone or general area. In some embodiments, when referring to a protein or protein module, a region may comprise a linear sequence of amino acids along the protein or protein module or may comprise a three dimensional area, an epitope and/or a cluster of epitopes. Some regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group, with or without modification or conjugation with one or more moiety or entity. C-termini refer to the end of a protein comprising an amino acid with a free carboxyl group, with or without modification or conjugation with one or more moiety or entity. N- and/or C-terminal regions may therefore comprise the N- and/or C-termini as well as surrounding amino acids. Some N- and/or C-terminal regions comprise from about 3 amino acids to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. Some C-terminal regions may comprise any length of amino acids that include the C-terminus, but do not comprise the N-terminus.

Region of antibody recognition: As used herein, the term "region of antibody recognition" refers to one or more regions on one or more antigens or between two or more antigens that are specifically recognized and bound by corresponding antibodies. Some regions of antibody recognition may comprise 1, 2, 3, 4, 5, 6, 7, 8, 9 or at least 10 amino acid residues. Regions of antibody recognition may comprise a junction between two proteins or between two domains of the same protein that are in close proximity to one another.

Sample: As used herein, the term "sample" refers to an aliquot or portion taken from a source and/or provided for analysis or processing. Samples may include histological or cytological specimens, tissue, bodily fluid and/or biopsies. Some samples may be from biological sources such as tissues, cells or component parts. Some samples may comprise bodily fluid samples. Body fluids samples may include but are not limited to blood, urine, mucous, amniotic fluid, saliva, lymphatic fluid, synovial fluid, cerebrospinal fluid, amniotic cord blood, vaginal fluid and semen. Some samples may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Some samples may comprise a medium, such as a nutrient broth or gel, which may contain cellular components, such as proteins or nucleic acid molecules.

Signal Sequences: As used herein, the phrase "signal sequences" refers to a sequence which can direct the transport or localization of a protein.

Stable: As used herein "stable" refers to a compound or entity that is sufficiently robust to survive isolation to a useful degree of purity from a reaction mixture. In some embodiments, stable compounds maintain a desired three-dimensional conformation or folding.

Stabilized: As used herein, the term "stabilize", "stabilized," "stabilized region" means to make or become stable. Stability may be measured relative to an absolute value. In some embodiments, stability is measured relative to a reference compound or entity.

Subject: As used herein, the term "subject" refers to any organism to which a kit or method of the present invention may be applied, e.g., for experimental, diagnostic, prophylactic, and/or therapeutic purposes. Typical subjects include animals (e.g., mammals such as mice, rats, rabbits, non-human primates, and humans) and/or plants. As referred to herein, "subject samples" comprise samples derived from one or more subject.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. Some individuals susceptible to a disease, disorder, and/or condition will develop the disease, disorder, and/or condition. Some individuals who are susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to extending survival and inhibiting growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control. Section and table headings are not intended to be limiting.

EXAMPLES

Example 1. Reduced synthetic surrogate compound synthesis

Reduced synthetic protein standards for use as surrogate compounds were synthesized according to the following methods. Equimolar amounts of Ac-ACNFNDVTTRLRENELTYYCAAK-NH$_2$ (SEQ ID NO:5) comprising a disulfide bond between cysteine residues 2 and 20 (corresponding to residues 39 and 63 of mature CD59) and N-hydroxysuccinimidyl-75-N-(3-maleimidopropionyl)-amido-4,7,10,13,16,19,22,25,28,31,34,37,40,43,46,49,52,55,58,61,64,67,70,73-tetracosaoxapentaheptacontanoate also known as MAL-DPEG®24-NHS ester, (Quanta Biodesign, Powell, Ohio;) Mol. Wt.: 1394.55 where the single compound discrete poly-(ethylene glycol) "DPEG®" Spacer (82 atoms and 95.2 Å) were dissolved in dimethyl sulfoxide (DMSO). Triethylamine was added portion wise to reach the pH to 7.0 and the reaction mixture was stirred at room temperature for 1 hour.

Figure 4:
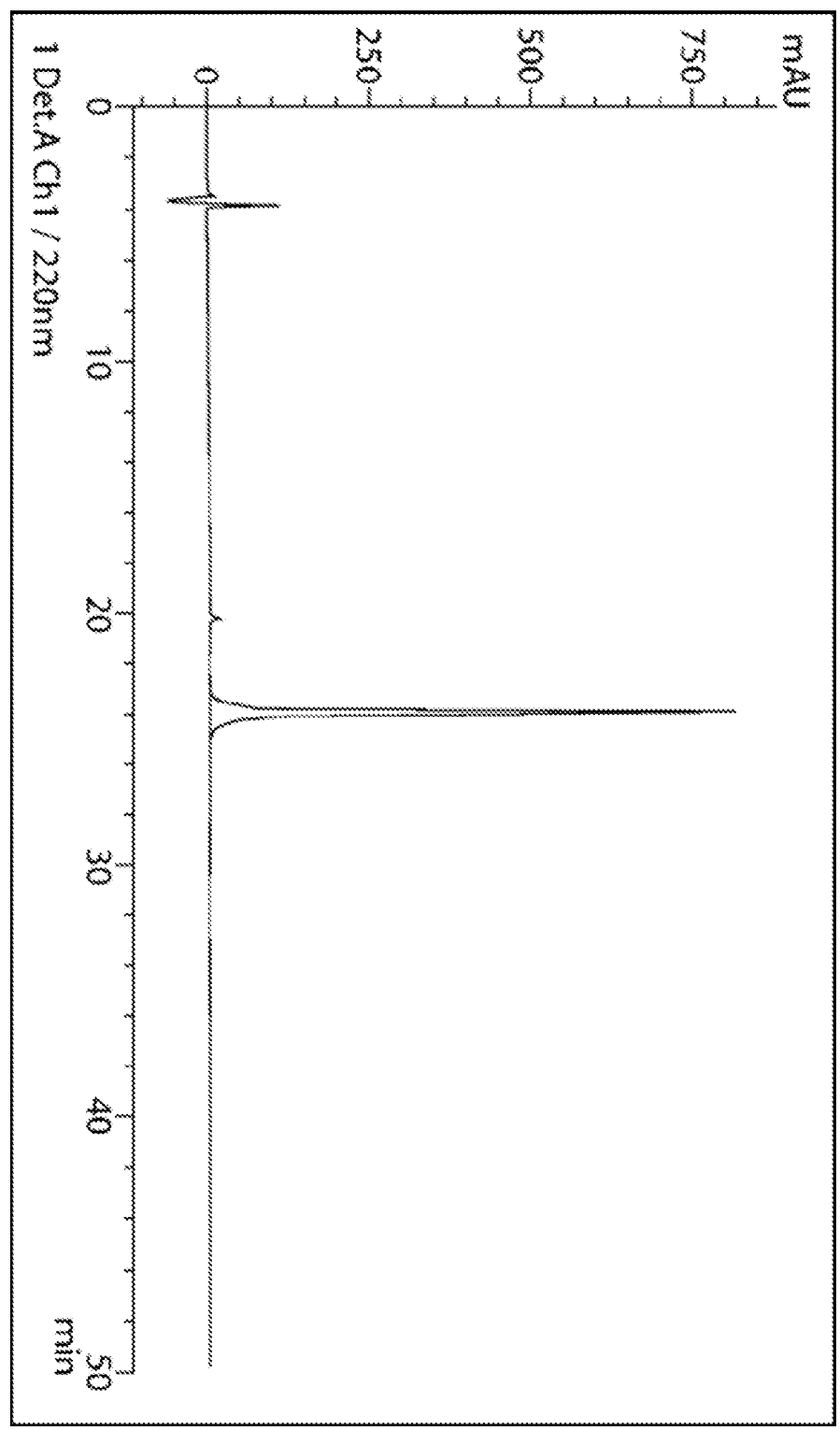
FIG. 4 depicts an HPLC trace for the hybrid peptide surrogate of posttranslationally modified: glycated and reduced hCD59-surrogate. Conditions: 0.50 mg in 500 µl $H_2O$/MeOH; Injection Volume: 36 µl; Gradient: 10-60% in 50 min.; Column: Jupiter 5u, C18, 300 Å, (4.6 mm i.d., 250 mL); Buffer: A: 0.05% TFA in $H_2O$; B: 0.05% TFA in MeCN; Flow: 1 mL/min.

Analytical high-performance liquid chromatography (HPLC) monitoring indicated the completion of reaction. To the above reaction mixture was then added one equivalent of Ac-NKAWKFEHANFNDC-OH (SEQ ID NO: 11) wherein K5, corresponding to K41 of the mature CD59, comprised glucitollysine and stirring was continued for one hour. Analytical HPLC monitoring indicated the disappearance of the reactants and formation of a new peak. The product was purified by HPLC with a LC-60 Luna Prep C18 column, 10 µm, 60×300 mm, using isocratic conditions to load compound (5% B for 10 min, then 15% for 5 min), then a linear gradient of 15-45% A in B in 60 min, where A=0.05% trifluoroacetic acid (TFA) in acetonitrile and B=0.05% TFA in water) at a flow rate=100 mL/min. The desired product was obtained at purity >97%. The amino acid analysis gave the following results (calcd.): Ala 5.2 (5); Arg 1.8 (2); Asp 8.1 (8); Glu 3.2 (3); His 0.82 (1); Leu 1.9 (2); Lys 2.1 (2); Phe 3.0 (3); Thr 2.9 (3); Tyr 2.0 (2); Val 1.0 (1). See FIG. 4.

Example 2. Amadori-Containing Surrogate Compound Synthesis

Amadori-containing synthetic protein standards comprising surrogate compounds are synthesized according to the following methods. Equimolar amounts of Ac-ACNFNDVTTRLRENELTYYCAAK-NH$_2$ (SEQ ID NO:5) comprising a disulfide bond between cysteine residues 2 and 20 (corresponding to residues 39 and 63 in the mature CD59) and MAL-DPEG®24-NHS ester (Mol. Wt.: 1394.55; single compound DPEG® Spacer is 82 atoms and 95.2 Å; Quanta Biodesign) are dissolved in DMSO. Triethylamine is added portion wise to reach the pH to 7.0 and the reaction mixture is stirred at room temperature for 1 hour.

Analytical HPLC monitoring indicates the completion of reaction. To the above reaction mixture is added one equivalent of Ac-NKAWKFEHANFNDC-OH (SEQ ID NO: 11) wherein K5 (corresponding to K41 of the mature CD59) is glycated, comprising an Amadori product, and stirring is continued for one hour. Analytical HPLC monitoring indicates the disappearance of the reactants and formation of a new peak. The product is purified by HPLC with a LC-60 Luna Prep C18 column, 10 µm, 60×300 mm, using isocratic conditions to load compound (5% B for 10 min, then 15% for 5 min), then a linear gradient of 15-45% A in B in 60 min, where A=0.05% TFA in acetonitrile and B=0.05% TFA in water) at a flow rate=100 mL/min. The desired product is then obtained.

Example 3. GCD59 Sandwich ELISA with Samples Pretreated with a Reducing Agent

The GCD59 sandwich enzyme-linked immunosorbent assay (ELISA) measures serum or plasma GCD59. The basic elements include anti-CD59 murine monoclonal antibody 4466 (10A7) as a capture antibody, anti-glucitollysine rabbit monoclonal antibody (clone 42) as a detection antibody, goat anti-rabbit IgG-H&I cross absorbed antibody, horseradish peroxidase (HRP)-conjugated (Bethyl Laboratories, Montgomery, Tex.) as a secondary detection antibody and a synthetic glycated CD59 surrogate compound used as a protein standard comprising two CD59 domains connected by a linker. Plates are coated with capture antibody. To carry this out, capture antibody is diluted in 1× Dulbecco's phosphate-buffered saline (DPBS; Lonza, Basel, Switzerland) to a final concentration of 3 ag/ml. Wells of Immulon 4HBX plates (Thermo Fisher, Waltham, Mass.) are coated with 100 µl of 3 µg/ml capture antibody solution. The plates are then incubated at 4° C. overnight under shaking conditions for a minimum of 16 hours. The next morning, plates are washed 3 times with plate washing buffer (Buffer D) comprising 1× phosphate buffered saline (PBS; Lonza, Basel, Switzerland) with 0.05% TWEEN®-20 (BioRad Laboratories, Hercules, Calif.). Plates are then blocked with protein free blocking buffer (Buffer B) in PBS, pH 7.4 (Thermo Scientific, Waltham, Mass.) at room temperature for 1 hour under shaking conditions. Plates are washed again, 2 times with Buffer D and are air dried at room temperature for 2 hours, wrapped in polyvinyl chloride (PVC) film wrap (VWR International, Radnor, Pa.) and stored at −20° C.

Serum or plasma samples are analyzed fresh or thawed from aliquots stored at −80° C. Frozen samples are thawed in a water bath at 37° C., vortexed and placed on ice until use in the assay. Fresh and thawed samples are then reduced with sodium borohydride (NaBH$_4$; Sigma-Aldrich, St. Louis, Mo.). For reduction, 50 μl aliquots from each sample are placed into microcentrifuge tubes (VWR International, Radnor, Pa.) and combined with 2.5 μl of freshly prepared IM NaBH$_4$. Samples are then incubated for 1 hour at room temperature before quenching with 1 ml of 1% acetic acid (VWR International, Radnor, Pa.). Samples are mixed thoroughly by pipetting, followed by vortexing. The resulting sample mixture comprises a 5% concentration of the original sample. Diluted samples are further diluted by combining 200 μl from each with 800 μl of Buffer C, comprising 10 mM ethylenediaminetetraacetic acid (EDTA; Sigma-Aldrich, St. Louis, Mo.) and 1% NonIdet P40 (Sigma-Aldrich, St. Louis, Mo.,) and vortexing, resulting in a sample concentration of 1%. 200 μl of the resulting solution is added to 10 ml of Buffer C in a 15 ml BD Falcon Tube (Becton, Dickinson and Company, Franklin Lakes, N.J.) and mixed well by vortexing resulting in a final sample concentration of 0.02%.

Synthetic glycated CD59 surrogate compound samples are prepared from stock solutions. Stock solutions comprise 1 mg of surrogate compound standard dissolved in 1 ml of 1×PBS (Lonza, Basel, Switzerland) and aliquoted into 100 single-use microfuge tubes, 10 μl into each tube. Stock solutions may be stored at −80° C. until use. For the production of a standard calibration curve, synthetic glycated CD59 surrogate compounds used as protein standard stock solutions are used to prepare standard calibration curve concentrations of 3 ng/ml, 2 ng/ml, 1 ng/ml, 0.5 ng/ml, 0.25 ng/ml and 0.125 ng/ml in individual tubes. 100 μl of each concentration are analyzed in the assay in triplicate.

Before adding diluted samples and standards, capture antibody-coated plates are warmed to room temperature for about 30 minutes. 100 μl of each diluted sample and prepared standard are added to plate wells and plates are then incubated for 1 hour at room temperature with shaking. Plates are then washed 4 times with Buffer D and blotted on paper towels to remove excess wash buffer. Buffer A, comprising protein free T20 blocking buffer, pH 7.4; (Thermo Fisher, Waltham, Mass.) is diluted 1:10 in 1×PBS and used to dilute detection antibody to a final concentration of 2.5 ag/ml. Diluted detection antibody solution is then added to each well of the assay plates and incubated for 2 hours at room temperature with shaking. Plates are then washed 4 times with Buffer D and blotted on paper towels to remove excess wash buffer.

0.5 ag/ml stock solutions of secondary detection antibodies are diluted 1:35,000 in PBS comprising 10% Buffer A and 100 μl are added to each well of the assay plates. Plates are then incubated 1 hour at room temperature under shaking conditions. Plates are then washed 4 times with Buffer D.

Bound secondary detection antibodies are detected colorimetrically using HRP substrate. 1 step Ultra tetramethylbenzidine (TMB)-ELISA (Thermo Fisher, Waltham, Mass.) is incubated at room temperature for 5-6 hours prior to use. 100 μl is then added to each well and allowed to develop for 18 minutes at room temperature under shaking conditions. Reactions are then halted with 10% v/v sulfuric acid (VWR International, Radnor, Pa.). Absorbance values for each well are obtained through spectrophotometric analysis (Multiskan FC, Thermo Fisher, Waltham, Mass.) at 450 nm within 30 minutes of halting the reaction. Standard curves are generated using absorbance values obtained from synthetic glycated CD59 surrogate compounds used as protein standard samples by plotting the absorbance obtained against the known concentration for each.

GCD59 concentration values are presented as Standard Peptide Units (SPU). 1 SPU is defined as the OD reading corresponding to 1 ng/ml of the synthetic GCD59 surrogate compound as obtained in the standard curve used for calibration. Determination of the concentration of GCD59 in a sample expressed in SPU is carried out by identifying the concentration of the synthetic GCD59 surrogate compound on the standard curve that corresponds to the absorbance value measured for the sample in the ELISA plate.

Example 4. GCD59 Sandwich ELISA without Reducing Agent Pretreatment

Plates are first coated with capture antibody. To carry this out, capture antibody is diluted in 0.05M carbonate-bicarbonate buffer (Sigma-Aldrich, St. Louis, Mo.) to a final concentration of 3 μg/ml. Wells of Immulon 4HBX plates (Thermo Fisher, Waltham, Mass.) are coated with 100 μl of 3 μg/ml capture antibody solution. The plates are then incubated at 4° C. overnight under shaking conditions (for a minimum of 16 hours). The next morning, plates are washed 3 times with Buffer D and then blocked with Buffer B at room temperature for 1 hour under shaking conditions. Plates are washed again, 2 times with Buffer D and air dried at room temperature for 2 hours, wrapped in PVC film wrap (VWR International, Radnor, Pa.) and stored at −20° C.

Serum or plasma samples may be analyzed fresh or thawed from aliquots stored at −80° C. Samples are thawed in a water bath at 37° C., vortexed and placed on ice until use in the assay. Samples are diluted to 1% in Buffer C and vortexed prior to analysis. 200 μl of the resulting solution is added to 10 ml of Buffer C in a 15 ml BD Falcon Tube (Becton, Dickinson and Company, Franklin Lakes, N.J.) and mixed well by vortexing, resulting in a final sample concentration of 0.02%.

Synthetic glycated CD59 surrogate compound comprising an Amadori-modified lysine residue at position 5 of SEQ ID NO: 11, corresponding to K41 in the mature human CD59 lacking the signal and GPI signal sequences, is prepared from stock solutions for use as a protein standard. Stock solutions comprise 1 mg of synthetic glycated CD59 surrogate compound dissolved in 1 ml of 1×PBS (Lonza, Basel, Switzerland) and aliquoted into 100 single-use microfuge tubes, 10 μl into each tube. Stock solutions may be stored at −80° C. until use. For the production of a standard calibration curve, synthetic glycated CD59 surrogate compounds used as protein standard stock solutions are used to prepare standard calibration curve concentrations of 3 ng/ml, 2 ng/ml, 1 ng/ml, 0.5 ng/ml, 0.25 ng/ml and 0.125 ng/ml in individual tubes. 100 μl of each concentration are analyzed in the assay in triplicate.

Before adding diluted samples and surrogate compound standards, capture antibody-coated plates are warmed to room temperature for about 30 minutes. 100 μl of each diluted sample and prepared surrogate compound standard are added to plate wells and plates are then incubated for 1 hour at room temperature with shaking. Plates are then washed 4 times with Buffer D and blotted on paper towels to remove excess wash buffer. Buffer A is diluted 1:10 in 1×PBS and used to dilute detection antibody to a final concentration of 2.5 ag/ml. Diluted detection antibody solution is then added to each well of the assay plates and incubated for 2 hours at room temperature with shaking. Plates are then washed 4 times with Buffer D and blotted on paper towels to remove excess wash buffer.

0.5 ag/ml stock solutions of secondary detection antibodies are diluted 1:35,000 in PBS comprising 10% Buffer A and 100 µl is added to each well of the assay plates. Plates are then incubated 1 hour at room temperature under shaking conditions. Plates are then washed 4 times with Buffer D.

Bound secondary detection antibodies are detected colorimetrically using HRP substrate. 1 step Ultra TMB-ELISA (Thermo Fisher, Waltham, Mass.) is incubated at room temperature for 5-6 hours prior to use. 100 µl is then added to each well and allowed to develop for 18 minutes at room temperature under shaking conditions. Reactions are then halted with 10% v/v sulfuric acid (VWR International, Radnor, Pa.). Absorbance values for each well are obtained through spectrophotometric analysis (Multiskan FC, Thermo Fisher, Waltham, Mass.) at 450 nm within 30 minutes of halting the reaction. Standard curves are generated using absorbance values obtained from synthetic glycated CD59 surrogate compounds used as protein standard samples by plotting the absorbance obtained against the known concentration for each.

GCD59 concentration values are then obtained through extrapolation using the absorbance values obtained for each and comparing them against the standard curve generated using the synthetic glycated CD59 surrogate compounds used as protein standard values.

Example 5. Gestational Diabetes Study

Samples from pregnant patients were analyzed for GCD59 concentration. Samples were obtained from a cohort of 1600 subjects participating in "predictors of pre-eclampsia (POPs) study" conducted at the Brigham & Women's hospital from 2006-2008. Women in the POPs study were carefully monitored and followed by expert endocrinologists. 251 samples, from this cohort were from subjects in their 24$^{th}$ week of pregnancy. Of these, 54 had a diagnosis of GDM, while 197 did not. 101 samples were from the same subjects in their 35$^{th}$ week of pregnancy. These included samples from the 54 subjects diagnosed with GDM and 47 randomly selected from those subjects without a GDM diagnosis.

From those subjects analyzed, subjects with a diagnosis of GDM had a higher average age (34 years±5 years versus 31 years±5 years) weight (152 lbs±35 lbs versus 140 lbs±22 lbs) and body mass index (BMI, 28 kg/m$^2$±6 kg/m$^2$ versus 24 kg/m$^2$±4 kg/m$^2$).

Analyses of GCD59 concentration in these samples indicated a clear separation between subjects with and without a diagnosis of GDM at the 24 week time point (see FIG. 1). Further, GCD59 concentrations went down in samples taken at 35 weeks from subjects diagnosed with GDM, reflecting a response to treatment for the management of GDM.

Figure 2:
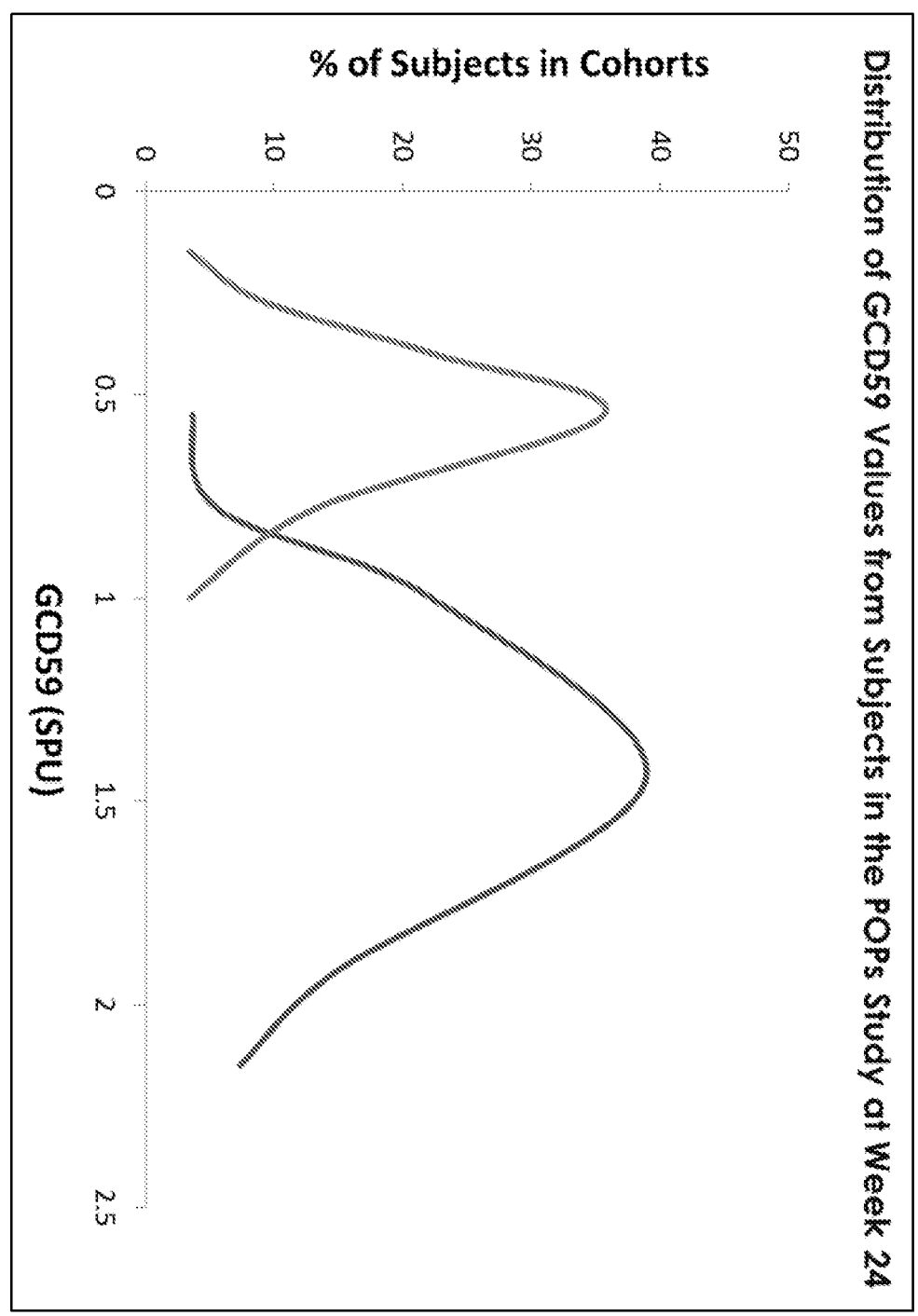
FIG. 2 depicts a graph showing the percentage of subjects in cohorts analyzed (pregnant subjects with or without gestational diabetes mellitus (GDM)) associated with increasing concentrations of GCD59.

FIG. 2 is a graph showing the percentage of subjects in the cohort analyzed comprising subjects diagnosed with GDM and those without a GDM diagnosis (Normals), associated with each concentration of GCD59.

Figure 3:
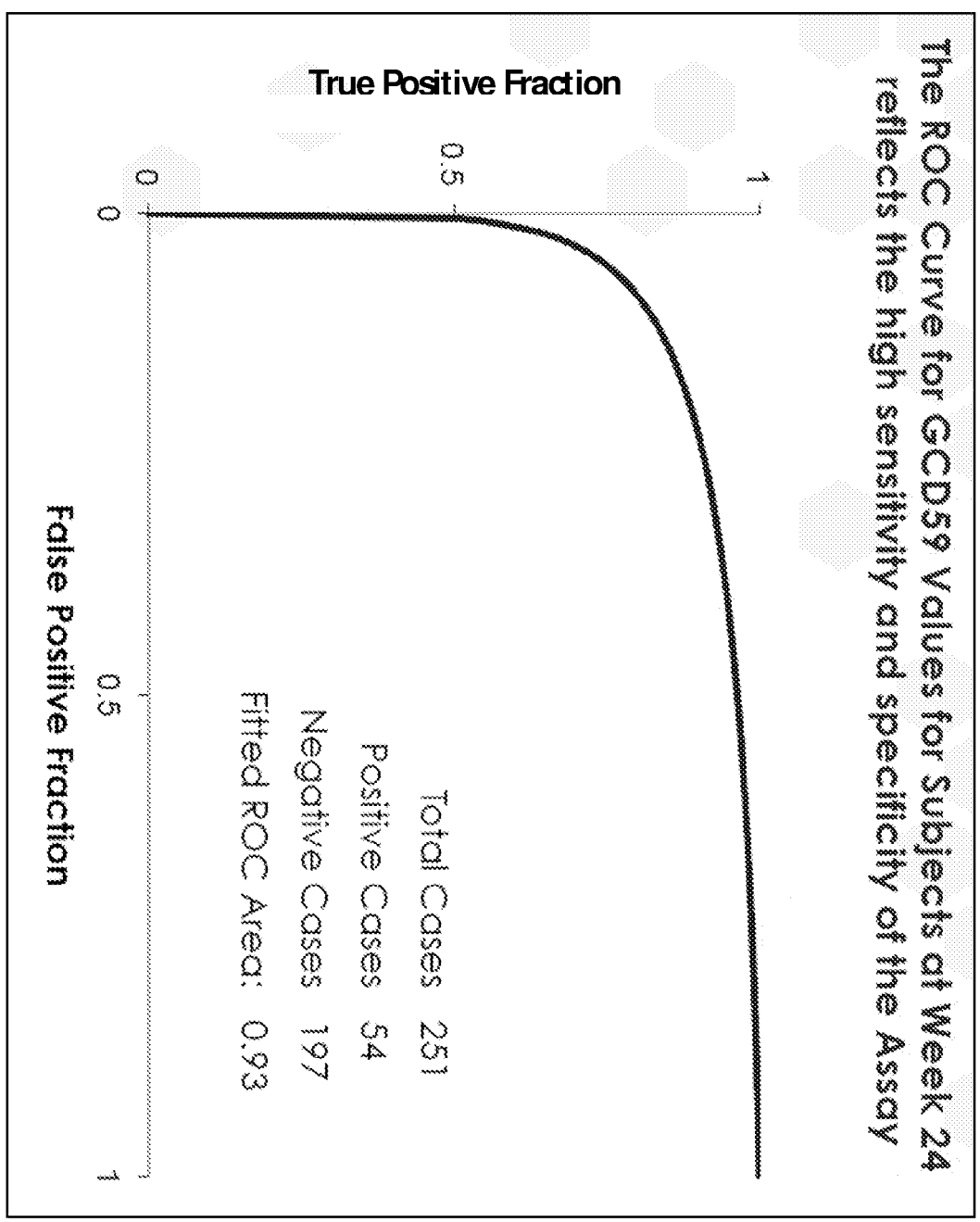
FIG. 3 depicts a graph showing a receiver operating characteristic (ROC) curve indicating the specificity and sensitivity with which GCD59 levels are able to detect pregnant subjects with GDM.

Conclusion: Results of the GCD59 ELISA indicate a clear differentiation between normal subjects and subjects suffering from GDM, with a sensitivity and specificity of greater than 90%. FIG. 3 is a graph showing a receiver operating characteristic (ROC) curve indicating the specificity with which GCD59 levels are able to detect pregnant subjects with GDM.

Example 6. Stratification of Pregnant Subjects 500 pregnant subjects are recruited. All subjects undergo standard blood glucose evaluations (including, but not limited to 100 g OGTT with 3 hour monitoring) as well as simultaneous analysis GCD59 levels between 22 and 24 weeks of pregnancy. With some subjects, follow-up measurements are conducted at week 35. Pre-term and post-natal metrics are evaluated for each subject. GCD59 levels are compared with blood glucose evaluations and other metrics to look for correlations. GCD59 levels are expected to correlate with blood glucose levels.

Example 7. Companion Diagnostic

A kit for the determination of GCD59 concentration levels is used as a companion diagnostic to facilitate and expedite drug development for anti-diabetic and metabolic disease drugs, aid in patient diagnosis, aid in patient monitoring and identify individuals at risk of developing disease-related complications. The kits are used to stratify subjects based on GCD59 concentration levels and select subjects for clinical trials. The kits are used to determine treatment type and dosages for subjects having or suspected of having pre-diabetes, diabetes or metabolic diseases.

Example 8. Risk Stratification

A kit for the detection and/or quantitation of GCD59 levels is used for stratifying subjects according to risk of developing diabetic complications. To correlate GCD59 levels with such risks, archival samples from epidemiological studies (including, but not limited to the landmark epidemiological Diabetes Complications Control Trial (DCCT)) are analyzed using the kit. Archival samples from the DCCT trial are analyzed. The DCCT was a major multicenter, randomized, clinical study conducted between 1983 and 1993 designed to assess whether intensive anti-diabetes treatment affects the onset or progression of early vascular complications occurring in patients afflicted with Type I diabetes. This trial involved 1,441 subjects from the United States and Canada (DCCT and EDIC: The Diabetes Control and Complications Trial and Follow-up Study. U.S. Department of Health and Human Services, National Institutes of Health. 2008 May. NIH Publication No. 08-3874). Samples are analyzed using the kit and correlated with metrics assessed in the trial. Correlations are used in future analyses to stratify subjects according to risk of developing diabetic complications using GCD59 levels.

Example 9. Prediction of Glycated Proteins

Glycated proteins such as human serum albumin, low-density lipoprotein, and CD59 (Table 2, entries 1-3, respectively) were reported in the literature (Ukita et al., *Clin. Chem.* (1991) 37:504; Johansen et al., *Glycobiol.* (2006) 16:844; and Davies et al., *J. Exp. Med.* (1989) 170:637). Those three literature references reported 1,823, 1,152, and 1,400 proteins in urine, respectively. By analyzing those three data sets, 658 proteins were identified to be common to all three studies (Marimuthu et al., *J. Proteome. Res.*, (2011) 10:2734; Adachi et al., *Genome. Biol.* (2006) 7:R80; and Li et al., *Rapid Commun. Mass Spectrom.* (2010)

24:823). Analyzing a sample of these 658 proteins with NetGlycate-1.0 software (www.cbs.dtu.dk/services/NetGlycate-1.0; and Johansen et al., *Glycobiol.* (2006) 16:844) predicted proteins of entries 1, 9, and 13-30 (Table 2) are likely to be glycated in urine. The analysis showed that any of the proteins of entries 1, 9, and 13-30 have at least one glycation potential score cutoff of >0.9 for at least one lysine.

Out of the 658 proteins, proteins of entries 4-12 (Table 2) were already found to be glycated in plasma and erythrocytes (Marimuthu et al., *J. Proteome. Res.*, (2011) 10:2734).

TABLE 2

List of exemplary glycated proteins

| Entry | Protein Description | Gene Symbol |
|---|---|---|
| 1 | Human serum albumin[1] | Alb[1] |
| 2 | Low-density liopoprotein[1] | LDL[1] |
| 3 | CD59[4] | CD59 |
| 4 | Hemopexin[2] | HPX[3] |
| 5 | Vitamin D binding protein[2] | GC[3] |
| 6 | Fibrinogen, alpha chain[2] | FGA[3] |
| 7 | Apolipoprotein A1[2] | APOA1[3] |
| 8 | Transferin[2] | TF[3] |
| 9 | Macroglobulin, alpha 2[2] | A2M[3] |
| 10 | Complement component 4A[2] | C4A[3] |
| 11 | Fibrinogen, beta chain[2] | FGB[3] |
| 12 | Fibrinogen, alpha chain[2] | FGA[3] |
| 13 | Abhydrolase domain-containing protein 1 4B | ABHD14B[3] |
| 14 | Amiloride-sensitive amine oxidase (copper-containing) precursor | ABP1[3] |
| 15 | Angiotensin-converting enzyme isoform 1 precursor | ACE[3] |
| 16 | Peptidase family M2 Angiotensin converting enzyme | ACE2[3] |
| 17 | Aconitase 1 | ACO1[3] |
| 18 | Lysosomal acid phosphatase isoform 1 precursor | ACP2[3] |
| 19 | Pancreatitis-associated protein | ACPP[3] |
| 20 | Alpha-actinin-4 | ACTN4[3] |
| 21 | Metalloproteinase with thrombospondin type 1 motifs | ADAMTS1[3] |
| 22 | Aspartylglucosaminidase | AGA[3] |
| 23 | Adenosylhomocysteinase | ACHY[3] |
| 24 | Alpha-2-HS-glycoprotein | AHSG[3] |
| 25 | Alcohol dehydrogenase (NADP$^+$) | AKR1A1[3] |
| 26 | Aldo-keto reductase family 1 | AKR1B1[3] |
| 27 | Aldehyde dehydrogenase family 1 member L1 | ALDH1L1[3] |
| 28 | Aldolase B, fructose-bisphosphate | ALDOB[3] |
| 29 | Amylase, alpha 2A (pancreatic) | AMY2A[3] |
| 30 | Apolipoprotein A4 | APOA4[3] |

[1]Ukita et al., *Clin. Chem.* (1991) 37: 504.
[2]Zhang et al., *J. Proteome. Res.*, (2011) 10: 3076.
[3]Marimuthu et al., *J. Proteome. Res.*, (2011) 10: 2734.
[4]Davies et al., *J. Exp. Med.* (1989) 170: 637.

Example 10. Use of Subject Samples as Internal Controls

Assays are conducted using internal controls, at three concentrations (low, medium and high) of GCD59, prepared from pooled plasma samples from individuals with diabetes. Values obtained from internal control samples are used to accept or reject individual ELISA analyses, according to pre-specified criteria following Westgard rules (Westgard J O, Barry P L, Hunt M R, et al. A multi-rule Shewhart chart for quality control in clinical chemistry. Clin Chem 1981; 27:493-501).

For assays comprising pretreatment with a reducing agent (according to Example 3,) internal control plasma samples are reduced, quenched and diluted to 1% for storage at –80° C. as previously described. Prior to continuing the assay, internal control samples are thawed and diluted to 0.2%, 0.1%, and 0.05%. Internal control samples are analyzed in duplicate on each assay plate.

For assays according to Example 4 (that do not require reducing agent treatment,) internal control plasma samples are diluted to 1% and stored at –80° C. as previously described. Prior to continuing the assay, internal control samples are thawed and diluted to 0.2%, 0.1%, and 0.05%. Internal control samples are analyzed in duplicate on each assay plate.

Example 11. Reducing Agent Solutions with Organic Solvents

Samples are prepared and analyzed according to the method of Example 3, with the exception of the sample reduction procedure. Serum or plasma samples are analyzed fresh or thawed from aliquots stored at –80° C. Frozen samples are thawed in a water bath at 37° C., vortexed and placed on ice until use in the assay. Fresh and thawed samples are then reduced with sodium borohydride (NaBH$_4$; Sigma-Aldrich, St. Louis, Mo.).

Reducing agent solutions comprise NaBH$_4$ in water or in an organic solvent selected from triethylene glycol dimethyl ether, tetraglyme and bis(2-methoxyethyl) ether. Reducing agent solutions with water comprise 1 M NaBH$_4$. Reducing agent solutions with triethylene glycol dimethyl ether comprise 2 M NaBH$_4$. Reducing agent solutions with tetraglyme comprise 3 M NaBH$_4$ and reducing agent solutions with bis(2-methoxyethyl) ether comprise 0.5 M NaBH$_4$ (Sigma-Aldrich, St. Louis, Mo.). Solutions of NaBH$_4$ in organic solvent at concentrations higher than 1 M are diluted in water by adding the organic solvent solution into water. Solutions of NaBH$_4$ in organic solvent at concentrations less than 1 M are used as is. Before combining reducing agent solutions with sample, solutions comprising triethylene glycol dimethyl ether or tetraglyme are diluted to 1 M with water.

For reduction, 50 µl aliquots from each sample are placed into microcentrifuge tubes (VWR International, Radnor, Pa.) and treated with 2.5 µl of 1 M NaBH$_4$ solutions or 5 µl of 0.5 M NaBH$_4$ solutions (or the volume that will furnish the equivalent of 2.5 µmol NaBH$_4$). Samples are then incubated for 1 hour at room temperature before quenching with 1 ml of 1% acetic acid (VWR International, Radnor, Pa.). Samples are mixed thoroughly by pipetting, followed by vortexing.

Example 12. Reducing Agent Solution Comparison

Normal (N) as well as diabetic (D) serum/plasma samples were thawed at room temperature and pooled within each group (to form an N pool and D pool). Pooled N and D samples were mixed by pipetting, vortexed and kept on ice. Samples were then subaliquoted, 50 µl each, to obtain 4 diabetic samples (D1-D4) and 4 normal samples (N1-N4). Working solutions were prepared for each of four NaBH$_4$ preparation formats according to Table 3. In the Table, MME refers to bis(2-methoxyethyl) ether TGDE refers to triethylene glycol diethyl ether and TG refers to tetraglyme. Stock solutions as well as NaBH$_4$ were purchased from Sigma-Aldrich (St. Louis, Mo.).

TABLE 3

| Preparation No. | Stock Solution | Working Solution |
|---|---|---|
| 1 | 0.5M NaBH$_4$ in MME | 0.5M (no dilution) |
| 2 | 2M NaBH$_4$ in TGDE | 1M (diluted with water) |
| 3 | 3M NaBH$_4$ in TG | 1M (diluted with water) |
| 4 | 1M NaBH$_4$ in water | 1M (no dilution) |

D1 and N1 samples were treated with 5 µl of preparation 1, D2 and N2 samples were treated with 2.5 µl of preparation 2, D3 and N3 samples were treated with 2.5 µl of preparation 3 and D4 and N4 samples were treated with 2.5 µl of preparation 4. Reactions were carried out for one hour at room temperature before being quenched with 1 ml of 1% acetic acid. Samples were mixed by pipetting resulting in a final solution comprising 5% reduced sample. Samples were then further diluted to 1% reduced sample by combining 200 µl of sample with 800 µl of serum dilution buffer. Serum dilution buffer was prepared by combining 15 ml protein free T20 blocking buffer (Thermo Fisher, Waltham, Mass.,) 10 ml of 0.5 M EDTA, 5 ml of NP40 and 470 ml of sterile water. Resulting solutions were vortexed for 15 seconds.

The 1% reduced sample was then subaliquoted into two 500 µl aliquots that were frozen at −80° C. until analysis.

ELISA analysis was carried out on the reduced samples according to the method of Example 3. GCD59 concentration values extrapolated from final absorbance readings are presented in Table 4 in Standard Peptide Units (SPU).

TABLE 4

| Sample | GCD59 (SPU) |
|---|---|
| D1 | 0.70 |
| D2 | 0.53 |
| D3 | 0.56 |
| D4 | 0.67 |
| N1 | 0.15 |
| N2 | 0.15 |
| N3 | 0.14 |
| N4 | 0.15 |

The results indicate that samples reduced with preparation 1 yield the highest level of detectable GCD59 with slightly higher detectable levels than samples treated with preparation 4.

The invention claimed is:

1. A kit for determining the concentration of GCD59 in a subject sample, said subject sample obtained from a pregnant subject, wherein said kit optionally comprises one or more internal controls and wherein said kit further comprises;
   a capture antibody capable of associating with a capture epitope on CD59, wherein said capture epitope does not comprise lysine residue number 41 (K41),
   a detection antibody capable of associating with a detection epitope on CD59, said detection epitope comprising glycated K41, wherein the glycated K41 is reduced to glucitollysine,
   a reducing agent solution comprising a reducing agent and an organic solvent, and
   a protein standard, wherein the protein standard comprises the detection epitope comprising the glycated K41, wherein the glycated K41 is reduced to glucitollysine.

2. The kit of claim 1, wherein said reducing agent is sodium borohydride.

3. The kit of claim 2, wherein said sodium borohydride is present in said reducing agent solution at a concentration of from about 0.1 M to about 10 M.

4. The kit of claim 2, wherein said organic solvent is bis(2-methoxyethyl) ether.

* * * * *

SEQUENCE LISTING

<160> NUMBER OF SEQ ID NOS: 11

<210> SEQ ID NO 1
<211> LENGTH: 77
<212> TYPE: PRT
<213> ORGANISM: Artificial Sequence
<220> FEATURE:
<223> OTHER INFORMATION: Synthetic Construct

<400> SEQUENCE: 1

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn
65                  70                  75

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct

<400> SEQUENCE: 2

Phe Glu His Cys Asn Phe Asn Asp Val Thr Thr Arg Leu Arg Glu Asn
1               5                   10                  15

Glu Leu Thr Tyr Tyr Cys Cys Lys Lys Asp Leu
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Phe Glu His Cys Asn Phe Asn Asp Val Thr Thr Arg Leu Arg Glu Asn
1               5                   10                  15

Glu Leu Thr Tyr Tyr Cys Cys Lys Lys
            20                  25

<210> SEQ ID NO 4
<211> LENGTH: 23
<212> TYPE: PRT
<213> ORGANISM: Artificial Sequence
<220> FEATURE:
<223> OTHER INFORMATION: Synthetic Construct

<400> SEQUENCE: 4

His Cys Asn Phe Asn Asp Val Thr Thr Arg Leu Arg Glu Asn Glu Leu
1               5                   10                  15

Thr Tyr Tyr Cys Cys Lys Lys
            20

<210> SEQ ID NO 5
<211> LENGTH: 23
<212> TYPE: PRT
<213> ORGANISM: Artificial Sequence
<220> FEATURE:
<223> OTHER INFORMATION: Synthetic Construct

<400> SEQUENCE: 5

Ala Cys Asn Phe Asn Asp Val Thr Thr Arg Leu Arg Glu Asn Glu Leu
1               5                   10                  15

Thr Tyr Tyr Cys Ala Ala Lys
            20

<210> SEQ ID NO 6
<211> LENGTH: 28
<212> TYPE: PRT
<213> ORGANISM: Artificial Sequence
<220> FEATURE:
<223> OTHER INFORMATION: Synthetic Construct

<400> SEQUENCE: 6

Ala Phe Glu His Cys Asn Phe Asn Asp Val Thr Thr Arg Leu Arg Glu
1               5                   10                  15

Asn Glu Leu Thr Tyr Tyr Cys Ala Ala Lys Asp Leu
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: bAla

<400> SEQUENCE: 7

Ala Phe Glu His Cys Asn Phe Asn Asp Val Thr Thr Arg Leu Arg Glu
1               5                   10                  15

Asn Glu Leu Thr Tyr Tyr Cys Xaa Lys Asp Leu
            20                  25

```
<210> SEQ ID NO 8
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Aib

<400> SEQUENCE: 8

Ala Phe Glu His Cys Asn Phe Asn Asp Val Thr Thr Arg Leu Arg Glu
1               5                   10                  15

Asn Glu Leu Thr Tyr Tyr Cys Xaa Ala Lys Asp Leu
            20                  25

<210> SEQ ID NO 9
<211> LENGTH: 14
<212> TYPE: PRT
<213> ORGANISM: Artificial Sequence
<220> FEATURE:
<223> OTHER INFORMATION: Synthetic Construct

<400> SEQUENCE: 9

Asn Lys Cys Trp Lys Phe Glu His Cys Asn Phe Asn Asp Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Asn Lys Ala Trp Lys Phe Glu His Ala Asn Phe Asn Asp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

Asn Lys Ala Trp Lys Phe Glu His Ala Asn Phe Asn Asp Cys
1               5                   10
```